United States Patent [19]

Weiner et al.

[11] Patent Number: 5,556,744
[45] Date of Patent: Sep. 17, 1996

[54] METHODS AND COMPOSITIONS FOR DIAGNOSING AND TREATING CERTAIN HIV INFECTED PATIENTS

[75] Inventors: David B. Weiner, Merion Station; Kenneth E. Ugen, Philadelphia; William V. Williams, Havertown, all of Pa.

[73] Assignees: The Trustees of the University of Pennsylvania; The Wistar Institute of Anatomy & Biology, both of Philadelphia, Pa.

[21] Appl. No.: 218,025

[22] Filed: Mar. 24, 1994

Related U.S. Application Data

[63] Continuation-in-part of Ser. No. 891,451, May 29, 1992, abandoned.

[51] Int. Cl.$^6$ ........................................... C12Q 1/70
[52] U.S. Cl. .................. 435/5; 435/7.1; 435/974; 435/975; 530/324; 530/325; 530/326; 530/327; 530/328; 530/826
[58] Field of Search ........................ 435/5, 7.1, 974, 435/975; 530/324–328, 826

[56] References Cited

FOREIGN PATENT DOCUMENTS

| | | |
|---|---|---|
| 273716 | 7/1988 | European Pat. Off. . |
| 279688 | 8/1988 | European Pat. Off. . |
| 306219 | 3/1989 | European Pat. Off. . |
| 328403 | 8/1989 | European Pat. Off. . |
| 330359 | 8/1989 | European Pat. Off. . |
| 462551 | 12/1991 | European Pat. Off. . |
| 471407 | 2/1992 | European Pat. Off. . |
| WO91/04273 | 4/1991 | WIPO . |

OTHER PUBLICATIONS

Geysin et al, "Cognitive features of continuous antigenic determinants", *J. Molecular Recognition*, vol. 1 No. 1 (Feb. 1988) pp. 32–41.

LaRosa et al, *Science*, vol. 249, pp. 932–935, 24 Aug. 1990.

Warren et al, *Journal of Virology*, vol. 64(2) pp. 486–492 Feb. 1990.

K. Ugen et al, "Vertical Transmission of Human Immuno-deficiency Virus (HIV) Infection—Reactivity of Maternal Sera with Glycoprotein 120 and 41 Peptides from HIV Type 1", *J. Clin. Invest.*, 89:1923–1930 (Jun. 1992) [Ugen I].

K. Ugen et al, "Vertical Transmission of HIV Infection: Maternal Humoral Immune Responses to gp120 and gp41 Peptides", *Vaccines 92*, pp. 183–189, Cold Spring Harbor Laboratory Press (Apr. 3, 1992) [Ugen II].

P-A. Broliden et al, "Diagnostic Implication of Specific Immunoglobulin G Patterns of Children Born to HIV-infected Mothers", *AIDS*, 3:577–582 (Sep. 1989) [Broliden I].

P-A. Broliden et al, "Identification of Human Neutralization-Inducing Regions of the Human Immuno-deficiency Virus Type 1 Envelope Glycoproteins", *Proc. Natl. Acad. Sci. USA*, 89(2):461–465 (Jan. 15, 1992) [Broliden II].

Y. Devash et al, "Vertical Transmission of Human Immuno-deficiency Virus is Correlated with the Absence of High-Affinity/Avidity Maternal Antibodies to the gp120 Principal Neutralizing Domain", *Proc. Natl. Acad. Sci. USA*, 87(9):3445–3449 (May 1990) [Devash I].

Y. Devash et al, "C-Terminal Fragments of gp120 and Synthetic Peptides from Five HTLV–III Strains: Prevalence of Antibodies to the HTLV–III–MN Isolate in Infected Individuals", *AIDS Research and Human Retroviruses*, 6(3):307–316 (Apr. 4, 1990) [Devash II].

(List continued on next page.)

*Primary Examiner*—Christine M. Nucker
*Assistant Examiner*—Jeffrey Stucker
*Attorney, Agent, or Firm*—Howson and Howson

[57] ABSTRACT

The present invention provides a panel of HIV peptides useful in diagnosing whether or not a patient is of vertical HIV transmission status, methods for diagnosing same, methods for identifying epitopes and peptides associated with non-transmission status, and pharmaceutical and vaccine compositions containing same.

2 Claims, 3 Drawing Sheets

OTHER PUBLICATIONS

P. Rossi et al, "Presence of Maternal Antibodies to Human Immunodeficiency Virus 1 Envelope Glycoprotein gp120 Epitopes Correlates with the Uninfected Status of Children Born to Seropositive Mothers", *Proc. Natl. Acad. Sci. USA*, 86:8055–8058 (Oct. 1989) [Rossi I].

J. Goedert et al, "Mother–to–Infant Transmission of Human Immunodeficiency Virus Type 1: Association with Prematurity or Low Anti–gp120", *The Lancet*, pp. 1351–1354 (Dec. 9, 1989).

P. Rossi, "Maternal Factors Involved in Mother–to–Child Transmission of HIV–1", *J. Acq. Imm. Def. Syn.*, 5(10):1019–1029 (Nov. 1992) [Rossi II].

C. Robertson et al, "Maternal Antibodies to gp120 V3 Sequence do not Correlate with Protection Against Vertical Transmission of Human Immunodeficiency Virus", *J. Infect. Dis.*, 166(4):704–709 (Oct. 1992).

S. Wolinsky et al, "Selective Transmission of Human Immunodeficiency Virus Type–1 Variants from Mothers to Infants", *Science*, 255:1041–1180 (Feb. 28, 1992).

J. Cotropia et al, "Characterization of Human Monoclonal Antibodies to the HIV–1 Transmembrane gp41 Protein", *Vaccines92*, pp. 157–163, Cold Spring Harbor Laboratory Press (Jul. 21, 1992).

D. McPhee et al, "Recognition of Envelope and tat Protein Synthetic Peptide Analogs by HIV Positive Sera or Plasma", *FEBS Letter*, 233(2):393–396 (Jun. 1988).

D. van Tijn et al, "Antigenicity of Linear B–Cell Epitopes in the C1, V1, and V3 Region of HIV–1 gp120", *J. Acq. Imm. Def. Syn.*, 2(3):303–306 (Jun. 1989).

P. Tijssen, "Practice and Theory of Enzyme Immunoassays", *Laboratory Techniques in Biochemistry and Molecular Biology*, 15:9–21, 329–384 (Aug. 1985).

J. Krowka et al, "Epitopes of Human Immunodeficiency Virus Type 1 (HIV–1) Envelope Glycoproteins Recognized by Antibodies in the Sera of HIV–1–Infected Individuals", *Clin. Immunol. Immunopath.*, 59(1):53–64 (Apr. 1991).

K. Takahashi et al, "Specific Lysis of Human Immuno–deficiency Virus Type 1–Infected Cells by a HLA–A3.1–Restricted CD8+ Cytotoxic T–lymphocyte Clone that Recognizes a Conserved Peptide Sequence within the gp41 Subunit of the Envelope Protein", *Proc. Natl. Acad. Sci. USA*, 88(22):10277–10281 (Nov. 15, 1991).

S. Modrow et al, "Carrier–Bound Synthetic Peptides Use as Antigen in HIV–1 ELISA Tests and in Antiserum Production", *J. Immunol. Meth.*, 118(1):1–7 (Mar. 1989).

J. Berzofsky et al, "Construction of Peptides Encompassing Multideterminant Clusters of Human Immunodeficiency Virus Envelope to Induce in vitro T Cell Responses in Mice and Humans of Multiple MHC Types", *J. Clin. Invest.*, 88:876–884 (Sep. 1991).

D. Davis et al, "The Immunodominance of Epitopes within the Transmembrane Protein (gp41) of Human Immunodeficiency Virus Type 1 may be Determined by the Host's Previous Exposure to Similar Epitopes on Unrelated Antigens", *J. Gen. Virol.*, 71(9): 1975–1983 (Sep. 7, 1990).

J. Hunt et al, "Discrimination Between HIV–1 and HIV–2–Seropositive Individuals Using Mouse Monoclonal Antibodies Directed to HIV Transmembrane Proteins", *AIDS Research and Human Retroviruses*, 6(7): 883–898 (Jul. 1990).

B. Wahren et al, "HIV–1 Peptides Induce a Proliferative Response in Lymphocytes from Infected Persons", *J. Acq. Imm. Def. Syn.*, 4:448–456 (May 1989).

A. Vahlne et al, "Immunizations of Monkeys with Synthetic Peptides Disclose Conserved Areas on gp120 of Human Immunodeficiency Virus Type 1 Associated with Cross––Neutralizing Antibodies and T–Cell Recognition", *Proc. Natl. Acad. Sci. USA*, 88(23):10744–10748 (Dec. 1, 1991).

N. Shaffer et al, "Maternal Antibodies to V3 Loop Peptides of gp120 are not Associated with Lack of Perinatal HIV–1 Transmission", Abstract No. W.C. 48, VII International Conference on AIDS: Science Challenging AIDS, Florence, Italy (Jun. 1991).

J–P. Allain et al, "Antibody to V3 Loop Peptide does not Predict Vertical Transmission of HIV", Abstract No. W.C.3263, VII International Conference on AIDS: Science Challenging AIDS, Florence, Italy (Jun. 1991).

K. Ugen et al, "Vertical Transmission of Human Retroviral Infections: Immunological Parameters", Archives of STD/HIV Research, 8:283–292 (Nov., 1994).

METHODS AND COMPOSITIONS FOR DIAGNOSING AND TREATING CERTAIN HIV INFECTED PATIENTS

This invention was made with the financial assistance of National Institutes of Health Grant No. NIH-RFA1231352685A1. The United States Government has certain rights in this invention.

CROSS-REFERENCE TO RELATED APPLICATION

This is a continuation-in-part of U.S. patent application Ser. No. 07/891,451, filed May 29, 1992, abandoned.

1. Field of the Invention

This invention relates generally to methods for diagnosis, treatment and prophylaxis of certain HIV infections.

2. Background of the Invention

The human immunodeficiency virus (HIV) is the etiologic agent of the acquired immunodeficiency syndrome (AIDS) and related disorders [F. Barre-Sinoussi et al, *Science*, 220:868–870 (1983); and R. C. Gallo et al, *Science*, 220:865–867 (1984)]. HIV-1 evades immune surveillance by multiple mechanisms including the inhibition of immune responsiveness through deletion of T helper CD4+ cells and extensive variation of envelope proteins, gp120 and gp41 [W. C. Koff and D. F Hoth, *Science*, 241:426–432 (1988)]. In fact, the destruction and depletion of CD4+ cells through direct infection by HIV is a hallmark of this disease [H. C. Lane and A. S. Fauci, *Ann. Rev. Immunol.*, 3:477–500 (1985)]. This depletion of the T helper subset ultimately results in profound immunosuppression.

Progression to symptomatic disease states in HIV-infected individuals is correlated with lower humoral and in vitro T cell immune responses. The humoral immune response is an important component of protective immunity against a number of infectious agents. In many cases neutralizing antibodies (which, regardless of the mechanism employed, can inhibit the infection of healthy cells) are generated against the infectious agents. Most of the targets for neutralizing antibodies against HIV-1 reside on the viral envelope gene products (gp120 and gp41).

Several HIV-1 neutralization epitopes have been identified on the external membrane glycoprotein gp120. These include: (a) a region near the amino terminus which has been shown to be important for virus entry; (b) the V3 hypervariable loop; (c) the CD4 binding domain; and (d) a region which spans the carboxy terminus of gp120 and the amino terminus of gp41.

The gp41 transmembrane glycoprotein is involved in the fusion step between HIV and the target cell and it cannot be shed from the surface of virally infected cells. Several domains in the gp41 have been shown to elicit neutralizing antibodies [T. C. Chanh et al, *EMBO J.*, 5:3065–3071 (1986); A. G. Dalgleish et al, *Virol.*, 165:209–215 (1988); E. K. Thomas et al, *AIDS*, 2:25–29 (1988)].

Cell-free neutralization assays have been a useful in vitro methods for the analysis of the anti-HIV potential of hyperimmune animal sera or HIV+ sera. In several studies, neutralizing antibodies have been correlated with lesser manifestations and better clinical outcome. In addition, some studies have shown that decreasing neutralizing antibody titers indicate a poor prognosis [J. N. Weber et al, *Lancet*, 1:119–121 (1987); L. A. Sawyer et al, *AIDS Res. Hum. Retroviruses*, 6:341–356 (1990)]. However, other investigations have failed to demonstrate a clear correlation between neutralizing antibody activity and clinical state, prognosis or vertical transmission status [J. Goedert et al, cited above; L. K. Vujcic et al, *J. Infect. Dis.*, 157:1047–1050 (1988); I. Wendler et al, *AIDS Res. Hum. Retroviruses*, 3: 157–163 (1987); G. P. Faulkner-Valle et al, *Tumori.*, 72:219–224 (1986); K. Ljunggren et al, *J. Infect. Dis.*, 161:198–202 (1990)]. Anti-syncytial and group specific neutralization activity are observed more frequently in the asymptomatic patient population than in patients with AIDS. Several peptides corresponding to defined regions of the HIV envelope, including the V3 loop region of gp120, are able to induce protective immune responses in experimental animals.

Pediatric AIDS is an important medical problem [D. Barnes, *Science*, 232: 1589–1590 (1986)]. The timing and mechanism of viral infection of the fetus or neonate is being intensely investigated but is still incompletely understood. While most infected newborns appear clinically and immunologically normal at birth, studies support vertical transmission of HIV to the fetus in utero and to the neonate at the time of delivery or postpartum.

While it is unknown if free virus can cross the placenta, in utero transmission of HIV is supported by several studies. For example, HIV has been cultured, or HIV DNA detected, in aborted fetuses of less than 15 weeks of gestational age [S. Sprecher et al, *Lancet*, 2:288–289 (1986); E. Jovaisas et al, *Lancet*, 2:1129 (1985)]. HIV-1 infection has also been observed by immunochemical and molecular methods in villous trophoblastic derivatives, villous mesenchymal cells and embryonic blood precursors of an eight week gestational fetus [P. Pizzo et al, *Am. J. Med.*, 85 (Suppl 2A):195–202 (1988)]. Additionally, children can become infected despite delivery by Cesarean section [M. C. Cowan et al, *Pediatrics*, 73:382–386 (1984)].

Some children may be infected following exposure to maternal blood at the time of delivery. In addition, the exchange of blood prior to birth or at birth between the mother and infant has been documented. Infected maternal blood cells, i.e., lymphocytes, can be found postpartum in the circulation of some infants and these cells can support HIV infection in vitro. Postpartum infection has been documented in children exposed to breast milk [J. Ziegler et al, *Lancet*, 1 :896–897 (1985)].

Despite the evidence that HIV infection of children can occur in utero, 65–80% of all infants seem to escape infection [S. Lewis et al, *Lancet*, 335:565–568 (1990)]. Little is known about the immune responses that might affect perinatal transmission of HIV. There are data suggestive of a protective role for humoral immunity in vertical transmission of HIV infection. Four studies have suggested a correlation between the presence of certain maternal antibodies to regions of the V3 loop and a reduced incidence of infection in the infant [P. A. Broliden et al, *AIDS*, 3:577–582 (1989); P. Rossi et al, *Proc. Natl. Acad. Sci. USA*, 86:8055–8058 (1989); J. Goedert et al, *Lancet*, 2:1351–1354 (1989); and Y. Devash et al, *Proc. Natl. Acad. Sci. USA*, 87:3445–3449 (1990)]. In each study, the antibody measured was directed against the gp120 envelope protein. High titer anti-gp120 antibodies against conserved portions of the V3 hypervariable loop of gp120, and high affinity/avidity antibodies against the principal neutralizing domain (PND) of the V3 hypervariable loop have been identified as potential correlates of protection. Other investigators have been unable to confirm the association of non-transmission and high titered responses to V3 [A. Jean-Pierre et al, VII International Conference on AIDS, Abstract W. C. 3263., p 361 (1991) and B. N. Parkeh et al, *AIDS*, 5: 1179–1184 (1991)].

Maternal antibody may protect the fetus by reducing the quantity of infectious virus in the maternal circulation or by passive transfer of protective antibody to the fetus during the last 3-4 months of pregnancy. One report suggested an increased incidence of HIV infection in premature infants, who may have lower levels of passively acquired maternal antibody [I. Auger et al, *Nature,* 336:575-577 (1988)]. So far, no information is available to assess the ability of antibodies from an individual mother to neutralize or react with the virus variant transmitted to her own infant. Additionally, there has been no detailed analysis of the contribution of the humoral immune response to regions outside the V3 region and maternal HIV transmission.

There remains a need in the art for compositions and methods for identifying humoral immune responses useful as antibody therapy protective against the vertical transmission of HIV from mother to child and for immune based therapy and vaccinal compositions to prevent prenatal and perinatal transmission of HIV. There also remains a need to determine the likelihood that a given pregnancy in an HIV infected mother will result in infection of the fetus.

SUMMARY OF THE INVENTION

In one aspect, the present invention provides a collection or panel of HIV peptides, useful in determining whether or not an HIV infected woman will transmit HIV to her fetus in a given pregnancy and a diagnostic kit for use in clinical laboratories containing these peptides. Desirably, when in the diagnostic kit, the peptides of the collection are associated with a detectable label or label system, capable of providing a conventional diagnostic signal. The kit also contains a standard or control which demonstrates the recognition pattern of a known maternally transmissible serum with the same peptides. These peptide collections are useful in the diagnosis of female HIV patients likely to transmit the infection to their newborns, or in the diagnosis of HIV infection in newborns.

In another aspect, the present invention provides a method for determining whether or not an HIV infected woman will transmit HIV to her fetus in a given pregnancy. This method involves providing a biological sample from said HIV-infected patient, e.g., serum, screening said sample with a collection of HIV peptides as defined above, quantitatively determining the peptides recognized by said sample, and comparing said recognized peptides to the standard. Samples obtained from patients at a low risk for transmitting HIV to the fetus will react with about two to three times more peptides in the collection than recognized by the standard serum from a patient who transmits HIV to her fetus.

In still a further aspect, the invention provides a method for determining the risk of an HIV infection in an infant born to an HIV-infected mother, which consists of employing as a hybridization probe a panel of peptides, which may optionally be labelled, or a multivalent construct of this invention.

In still another aspect, the present invention provides a vaccine composition useful in preventing vertical transmission of HIV comprising a pharmaceutically acceptable carrier and at least one HIV peptide associated with non-transmissibility. Optionally, such a vaccine composition may contain, or be administered in conjunction with, other anti-HIV agents.

In a further aspect, the present invention provides a method of preventing vertical transmission of HIV comprising the step of administering to a pregnant woman a vaccine composition as defined above.

In a further aspect, the invention provides a vaccinal composition useful in conferring passive immunity against HIV infection comprising an antibody directed against a peptide associated with lack of vertical transmission of HIV and, a pharmaceutical composition of this invention.

Other aspects and advantages of the present invention are described further in the following detailed description of the preferred embodiments, thereof.

BRIEF DESCRIPTION OF THE DRAWINGS

Figures 2C, 2D:
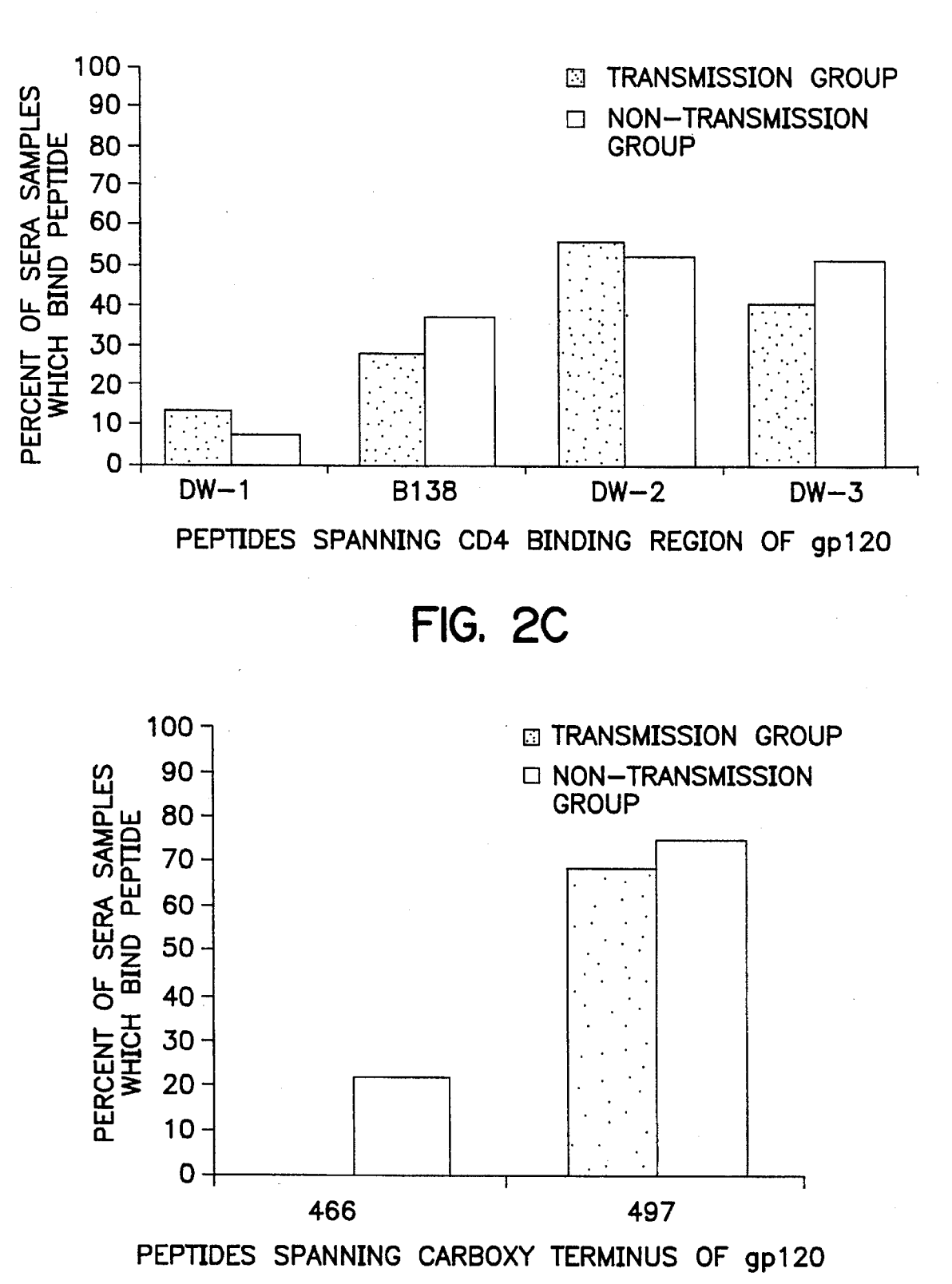

FIG. 2C is a bar graph illustrating the binding of maternal serum samples to peptides from the CD4-binding site of gp120. A closed box indicates the transmission group and an open box indicates the non-transmission group.

FIG. 2D is a bar graph illustrating the binding of maternal serum samples to peptides from the carboxyl terminus of gp120. A closed box indicates the transmission group and an open box indicates the non-transmission group.

DETAILED DESCRIPTION OF THE INVENTION

Figure 1:
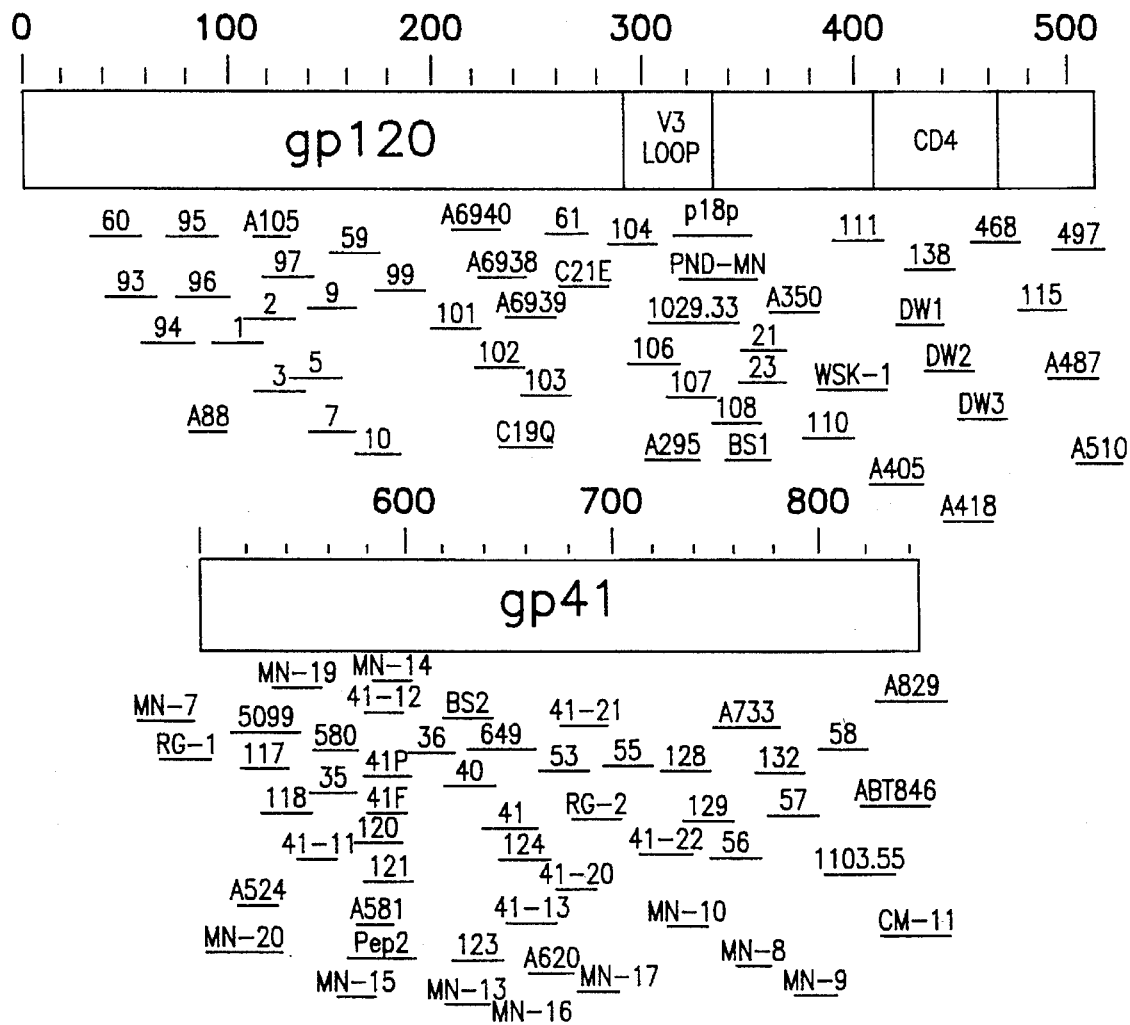
FIG. 1 provides a linear map of HIV gp120 and gp41 with the amino acid numbers above the map. The approximate location and the designation of the peptides described herein are shown in the map.
Figure 2A:
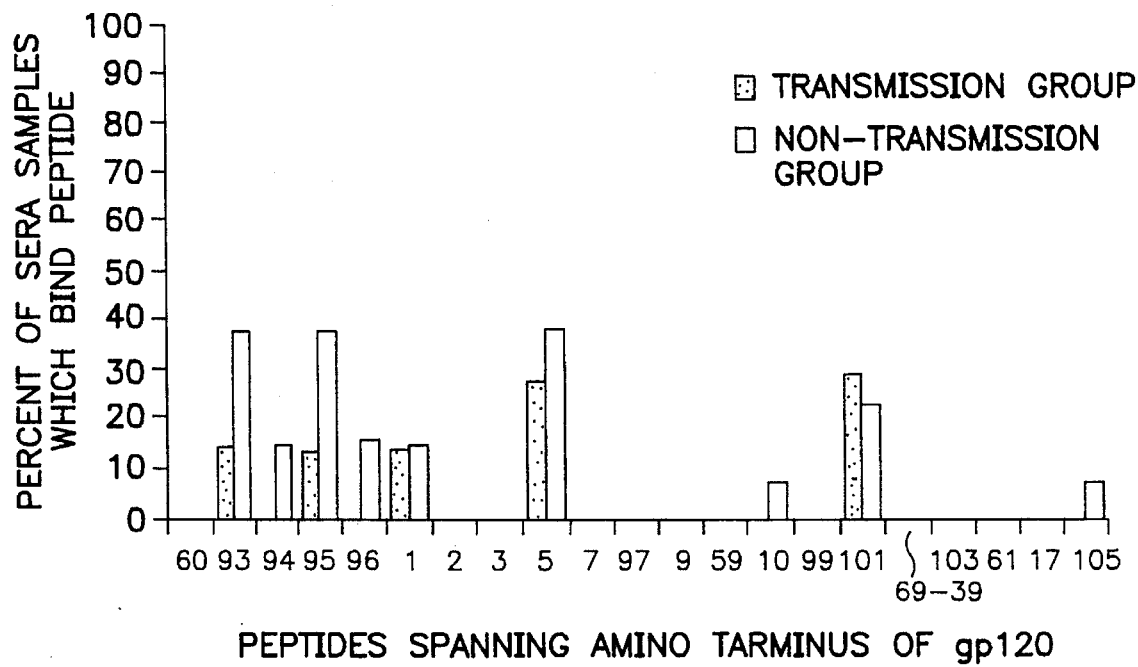
FIG. 2A is a bar graph illustrating the binding of maternal serum samples to peptides from the amino terminus of gp120. A closed box indicates the transmission group and an open box indicates the non-transmission group.
Figure 2B:
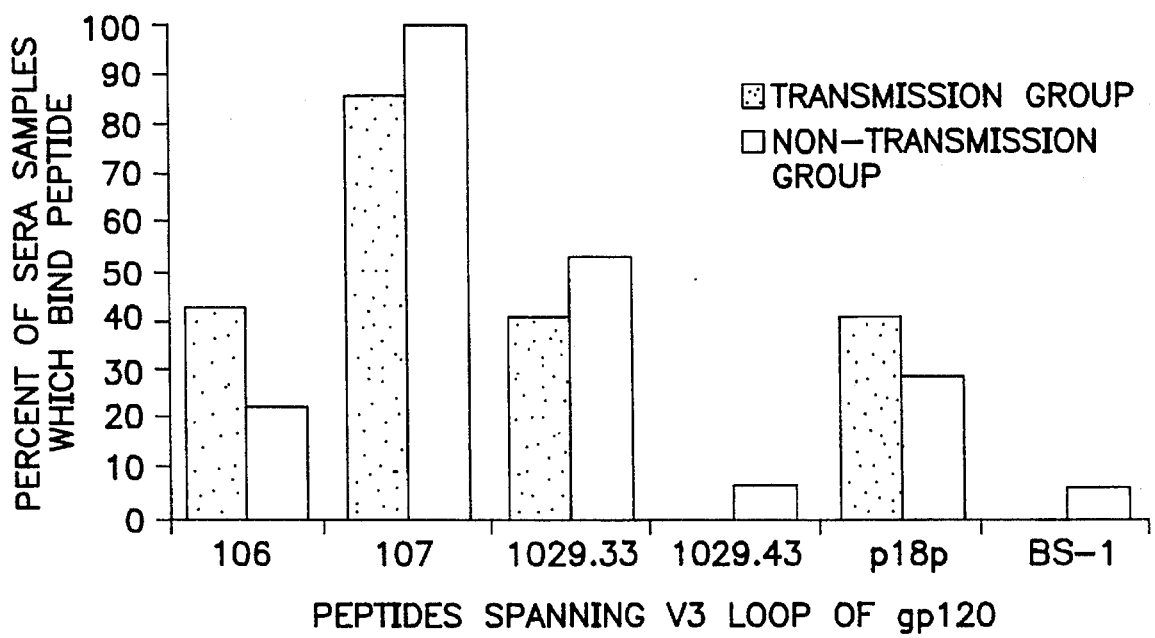
FIG. 2B is a bar graph illustrating the binding of maternal serum samples to peptides from the V3 loop of gp120. A closed box indicates the transmission group and an open box indicates the non-transmission group.

The present invention provides a collection or panel of HIV peptides useful in distinguishing between an immune maternal status which prevents transmission of HIV infection and immune status which permits maternal transmission of HIV infection (i.e., vertical transmission from mother to child). This invention also provides a means for identifying one or more of the peptides of this panel and/or the epitope(s) to which they correspond, which may, alone, be capable of distinguishing between maternal transmission and non-transmission immune status, and which may be useful in therapeutic and vaccinal compositions.

I. Definitions

As used herein, the term "panel" or "collection" of peptides refers to HIV peptides, fragments, and analogs thereof which, alone or preferably in combination with one another, are useful in identifying or distinguishing a biological sample as being associated with either lack of vertical transmission of HIV infection or the presence of vertical transmission of HIV infection. Preferably, this panel includes between about 5 to about 15 peptides derived from both gp41 and gp120 envelope proteins. More preferably, the panel includes about 10 peptides. Desirably, peptides of the panel are between about 8 to about 50 amino acids in length. More preferably, the peptides are between about 12 to about 20 amino acids in length. Such a collection or panel can include the specific HIV peptides identified in the lists and tables below, as well as other fragments of gp120 and gp41 from HIV isolates. Advantageously, when used in diagnosing whether or not an HIV-infected patient has an immune status which permits vertical transmission of HIV infection at any given time, e.g. during a pregnancy, a sample from a patient having an immune status which does not permit vertical transmission of HIV will recognize at least two-fold more of the peptides of a panel of the invention and exhibit a stronger immune response as reflected in higher antibody titers, as compared to a sample from a subject having an immune status which permits vertical transmission of HIV.

As used herein, the term "vertically transmissible HIV infection" or "transmitter", refer to a patient having an immune status which is such that it permits transmission of HIV infection to a fetus intraplacentally or to a newborn exposed to an HIV-infected mother's milk. The term "vertically non-transmissible HIV infection" or "non-transmitter" refer to a patient having an immune status which prevents vertical transmission of HIV infection.

As used herein, the term "fragment" refers to an amino acid sequence shorter than the HIV peptide from which it is derived, but which retains substantially identical biological activity of the intact peptide. Desirably such a fragment is at least four amino acids in length.

As used herein, the term "analog" refers to variations in the amino acid sequences of the HIV gp160 (gp120+gp41) proteins of this invention, which may typically include analogs that differ by only 1 to about 4 amino acid changes. Other examples of analogs include peptides or polypeptides with minor amino acid variations from the natural amino acid sequence of HIV peptides. In particular, the HIV peptides containing conservative amino acid replacements, i.e., those that take place within a family of amino acids that are related in their side chains, constitute analogs of this invention. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar conservative replacement of an amino acid with a structurally related amino acid will not have a significant effect on its activity, especially if the replacement does not involve an amino acid at an epitope of the polypeptides of this invention.

As used herein, the term "homologous peptide" includes peptide fragments which share at least 85% identity at the amino acid level, and preferably 95% identity, and substantially similar biological activity to a reference peptide.

As used herein, the term "standard" includes a pattern of peptide recognition of a sample screened against a selected panel or collection of peptides from a known transmitter, a known non-transmitter, or both. Alternatively, the suitable sample itself, e.g. sera, from transmitters or non-transmitters could be used as a standard.

II. HIV Peptides of the Invention

The following HIV peptides derived from strain HIV IIIB [ATCC CRL 8543] have been found to correlate significantly with lack of vertical transmission of HIV. These peptides are anticipated to be useful in the diagnostic panel, as well as in the therapeutic and vaccinal compositions of the invention.

(a) DYDTEVHNVWATHACV SEQ ID NO: 1
(b) RKSIGIQRGPGR SEQ ID NO: 2
(c) KQFINMWQEVGKAMYAPP SEQ ID NO: 3
(d) CFRPGGGDMRDNWREL SEQ ID NO: 4
(e) QNNLLRAIEAQQHLLQLTVWGI SEQ ID NO: 5
(f) CQNQQEKNEQELLEL SEQ ID NO: 6
(g) ELDKWASLWNWFNITNWLWY SEQ ID NO: 7
(h) VTRIVELLGRRGWEALKYWW SEQ ID NO: 8
(i) TLPCASDAKAYDTEV SEQ ID NO: 10
(j) FSYHRLRDLLLIVTR SEQ ID NO: 30,
(k) NATAIAVAEGTDRVIEVVQGAYRAI SEQ ID NO: 31,
(l) LGIWGCSGKLIC SEQ ID NO: 121,
(m) CNNKTFNGTGFCTNVSTVQ SEQ ID NO:137,
(n) VVQREKRAVGIG SEQ ID NO:133,
(o) YNKRKRIHIQRGPGRAFYTTKNII SEQ ID NO:134,
(p) KQIINMWQEVGKAMYA/CTRPNNNTRK-SIRIQRGPG SEQ ID NO:194
(q) YIKIFIMIVGGLVG SEQ ID NO:170
(r) DTSGRLVHGFLAIIW SEQ ID NO:159
(s) HIPTRIRQGLERALL SEQ ID NO:171 and
(t) HMLQLTVWGIKQLQAR SEQ ID NO:165.

Other peptide fragments which are particularly suitable for inclusion in the peptide collection of the invention are illustrated topographically in FIG. 1. The location and strain derivation of these peptides are provided in Tables 2, 9 and 12 below. Further, peptides of the V3 region are also expected to be useful in the peptide collection and methods of the invention. See, SEQ ID NO: 179 to 190. Also expected to be useful in the collection/panel of the invention are the peptides provided in SEQ ID NO:32 through SEQ ID NO:98. Additionally, other suitable peptide fragments identified by SEQ ID NOS, and the amino acid positions of the fragments corresponding with the gp160 sequence of each indicated strain are provided in Table 1 below.

TABLE 1

| Peptide Name | Amino Acids | HIV Strain | SEQUENCES |
|---|---|---|---|
| gp120 peptides | | | |
| A88 | 87–97 | MN | SEQ ID NO: 127 |
| A105 | 104–116 | MN | SEQ ID NO: 128 |
| [1]A295 | 295–321 | IIIB | SEQ ID NO: 129 |
| [1]A405 | 405–423 | Z3 | SEQ ID NO: 130 |
| [1]A418 | 418–441 | IIIB | SEQ ID NO: 131 |
| A487 | 481–503 | IIIB | SEQ ID NO: 132 |
| A510 | 505–516 | IIIB | SEQ ID NO: 133 |
| [1]PND-MN | 306–327* | MN/IIIB | SEQ ID NO: 134 |
| [1]A6938 | 200–217 | IIIB | SEQ ID NO: 135 |
| [1]A6940 | 223–238 | MN | SEQ ID NO: 136 |
| [2]C19Q | 228–246 | IIIB | SEQ ID NO: 137 |
| 115 | 473–487 | MN | SEQ ID NO: 138 |
| 110 | 391–405 | IIIB | SEQ ID NO: 139 |
| 102 | 211–225 | IIIB | SEQ ID NO: 140 |
| 108 | 327–341 | IIIB | SEQ ID NO: 141 |
| 104 | 275–289 | IIIB | SEQ ID NO: 142 |
| 61 | 251–272 | MN | SEQ ID NO: 143 |
| 21 | 343–357 | IIIB | SEQ ID NO: 144 |
| 23 | 261–275 | IIIB | SEQ ID NO: 145 |
| 111 | 401–415 | IIIB | SEQ ID NO: 146 |
| [1]C21E | 252–272 | MN | SEQ ID NO: 147 |
| [1]A350 | 350–378 | IIIB | SEQ ID NO: 148 |
| gp41 peptides: | | | |
| 41F | 598–605 | MN | SEQ ID NO: 149 |
| 41P | 599–606 | MN | SEQ ID NO: 150 |
| [2]41-12 | 579–604 | IIIB | SEQ ID NO: 151 |
| [1]41-21 | 661–683 | IIIB | SEQ ID NO: 152 |
| [2]41-13 | 616–632 | BRU | SEQ ID NO: 153 |
| [2]41-20 | 644–663 | IIIB | SEQ ID NO: 154 |
| [2]41-22 | 702–720 | BH10 | SEQ ID NO: 155 |
| 56 | 747–767 | IIIB | SEQ ID NO: 156 |
| [1]41-11 | 541–564 | MN | SEQ ID NO: 157 |
| MN-10 | 716–730 | MN | SEQ ID NO: 158 |
| MN-8 | 744–758 | MN | SEQ ID NO: 159 |

TABLE 1-continued

| Peptide Name | Amino Acids | HIV Strain | SEQUENCES |
|---|---|---|---|
| MN-9 | 758–772 | MN | SEQ ID NO: 160 |
| MN-7 | 490–513 | MN | SEQ ID NO: 161 |
| 5099 | 512–543 | IIIB | SEQ ID NO: 162 |
| A524 | 523–530 | MN | SEQ ID NO: 163 |
| MN-20 | 507–521 | MN | SEQ ID NO: 164 |
| MN-15 | 565–580 | MN | SEQ ID NO: 165 |
| MN-13 | 619–637 | MN | SEQ ID NO: 166 |
| MN-16 | 638–650 | MN | SEQ ID NO: 167 |
| MN-14 | 581–597 | MN | SEQ ID NO: 168 |
| MN-19 | 531–540 | MN | SEQ ID NO: 169 |
| MN-17 | 682–695 | MN | SEQ ID NO: 170 |
| CM-11 | 842–856 | MN | SEQ ID NO: 171 |
| A620 | 615–627 | IIIB | SEQ ID NO: 172 |
| 58 | 794–817 | IIIB | SEQ ID NO: 173 |
| A733 | 728–745 | IIIB | SEQ ID NO: 174 |
| A829 | 824–831 | IIIB | SEQ ID NO: 175 |
| BS-2 | 625–634 | IIIB | SEQ ID NO: 176 |
| RG-1 | 510–516 | IIIB | SEQ ID NO: 177 |
| RG-2 | 678–697 | IIIB | SEQ ID NO: 178 |
| CM-12 | 830–842 | MN | SEQ ID NO: 197 |

*Residues 306–327 are derived from the gp120 from HIV-1 MN strain. The QR is derived from HIV-1 IIIB strain and was inserted before the GPG tripeptide of the MN strain.
[1]Peptides available from NIH. See NIH AIDS Research and Reference Reagent Program, January 1994 Catalog, p. 120–123.
[2]Peptide referenced in AIDS Research and Reference Reagent Program, January 1991 Catalog, p. 153, 158, 159, 160, 162.

It is anticipated that peptide fragments homologous to the peptide fragments above and which are derived from other HIV strains will similarly correlate specifically with non-vertical transmission of HIV.

Other HIV strains are readily available from depositaries such as the American Type Culture Collection, as well as from academic and commercial sources. Particularly desirable are HIV isolates obtained from infected individuals, e.g. the HIV-I-MN isolate [Y. Devash et al, *AIDS Res. and Human Retroviruses*, 6(3):307–316 (1990)] or the SF-2 isolate. The IIIB (also known as HXB2), MN and SF-2 sequences can be found in the *Human Retroviruses and AIDS I-II*, ed. G. Meyers et al, p. IIA-40 through IIA-55 (August 1933). Another useful HIV strain, Z3, is described in K. M. Callahan et al, *J. Immunol.,* 144(9):3341–3346 (May 1, 1990). Additionally, the envelope sequences of strains MN and BH10 are also provided in C. Gurgo et al, *Virol.,* 164:531–526 (1988). These publications are incorporated by reference herein.

For use in the compositions and methods of this invention, it is anticipated that the above-described HIV peptides, fragments and analogs thereof, may be designed into conventionally known, alternative constructs to enhance the production of the peptide or its immunogenicity.

For example, multivalent constructs, e.g., associations of the HIV peptides characterized by multiple copies of a single peptide, or preferably, single or multiple copies of several of the above-described peptides may be designed [see, e.g., European Patent Application 0339695, published Nov. 2, 1989, incorporated by reference herein.]

In another form, the peptides may optionally be fused in frame or otherwise conventionally conjugated to a protein/peptide fusion partner. For example, one of skill in the art may design the HIV peptide in association with a selected fusion partner, such as the same or other HIV peptides of this invention, a preferred signal sequence, a sequence which is characterized by enhanced secretion in a selected host cell system (e.g., ubiquitin, α mating factor, beta-galactosidase and influenza proteins), a sequence which enhances the stability of the HIV peptide, or another peptide or protein which imparts desirable characteristics to the HIV peptide (e.g., tetanus toxoid, keyhole limpet hemocyanin (KLH), bovine serine albumin (BSA), hepatitis B virus core antigen, T cell epitopes). Such peptide or protein fusions may be mediated and preferentially distanced from each other, if desired, through a conventional linker sequence of between about 2 to about 50 amino acids in length. This linker sequence may encode, if desired, a polypeptide which is selectively cleavable or digestible by conventional chemical or enzymatic methods.

Similarly, the peptide of the invention may be associated with a non-protein carrier or compound such as a diagnostic label or immobilizing agent, a polystyrene bead or the like.

Moreover, it is possible, using the basic methods reviewed by L. Reichmann et al, *Nature,* 332:323 (1988), for a skilled artisan to engineer a peptide of the present invention as an epitope loop into an entire antibody or fragment thereof, e.g., chimeric antibodies.

This invention also encompasses the corresponding nucleotide sequences of the specifically-recited HIV peptides, fragments and multivalent constructs of this invention which are described herein. For example, one of skill in the art can readily determine the nucleotide sequences which encode the HIV peptides (a) through (t), as well as those sequences which encode the other peptide sequences of the invention, including those of FIG. 1. Additionally, the invention encompasses other DNA sequences of the peptides and polypeptides of this invention, such as allelic variations of DNA sequences encoding the various illustrated HIV amino acids, as well as deliberately modified analogs or derivatives thereof are also included in the present invention. Similarly, DNA sequences which code for peptide sequences of the invention but which differ in codon sequence due to the degeneracies of the genetic code or variations in the DNA sequence encoding these peptides which are caused by point mutations or by induced modifications to enhance the activity, half-life or production of the peptide encoded thereby are also encompassed in the invention. These sequences may be used in the recombinant production or chemical synthesis of the peptides by conventional means.

A. Production of HIV Peptides

The HIV peptides, fragments, and analogs thereof, and multivalent peptides, optionally associated with fusion partners of the invention, are preferably synthesized using conventional synthesis techniques, e.g., by chemical synthesis techniques. Alternatively, a skilled artisan may synthesize any of the peptides of the present invention by using an automated peptide synthesizer (e.g., an Applied Biosystems model 430A) using standard t-Boc chemistry as reported by L. A. Carpino, *J. Am. Chem. Soc.,* 79:4427 (1957), the disclosure of which is hereby incorporated by reference.

Alternatively, the peptides and other constructs of the invention may be prepared by known genetic engineering techniques, e.g., recombinant DNA techniques by cloning and expressing within a host microorganism or cell a DNA fragment carrying a coding sequence for the selected peptide or construct. Coding sequences for the HIV peptides, fragments and other proteins, e.g., fusion partners, can be prepared synthetically or can be derived from viral RNA by known techniques, or from available cDNA-containing plasmids.

Systems for cloning and expressing the HIV peptides or polypeptides in various microorganisms and cells, including, for example, *E. coli*, Bacillus, Streptomyces, Saccharomyces, mammalian, yeast and insect cells, and suitable vectors therefor are known and available from private and public laboratories and depositories and from commercial vendors. Currently, one preferred host is a mammalian cell. Suitable mammalian cells include Chinese Hamster ovary cells (CHO) or COS-1 cells. The selection of other suitable host cells and methods for transformation, culture, amplification, screening and product production and purification can be performed by one of skill in the art by reference to known techniques. See, e.g., Gething and Sambrook, *Nature*, 293:620–625(1981). Another known expression system includes the baculovirus expression system and vectors. While not preferred, *E. coli* may also be used for production of the HIV peptides and fragments, where the proper glycosylation and configuration is found to be achieved.

When produced by conventional recombinant means, the HIV peptides may be isolated either from the cellular contents by conventional lysis techniques or from cell medium by conventional methods, such as chromatography. See, e.g., Sambrook et al, *Molecular Cloning. A Laboratory Manual.*, 2d Edit., Cold Spring Harbor Laboratory, New York (1989).

Whether produced recombinantly or synthesized, the peptides of the invention may be purified using conventional means. Desirably, when used in the diagnostic panel of the invention, the peptides are at least about 85% pure. One of skill in the art can readily determine the appropriate level of purity required for the desired application for which the peptides are to be used.

B. Antibody Production

The present invention also provides antibodies capable of recognizing and binding naturally-occurring HIV epitopes on the peptides of the invention, when the virus or particles thereof are present in a biological fluid of a subject. These antibodies may be generated by conventional means utilizing the isolated peptides or multivalent peptide constructs of this invention [See, e.g., PCT published application WO91/04273, published Apr. 4, 1991]. For example, polyclonal antibodies may be generated by conventionally stimulating the immune system of a selected animal with one or more of the above-identified peptides, or multivalent constructs, allowing the immune system to produce natural antibodies thereto, and collecting these antibodies from the animal's blood or other biological fluid. High titer polyclonal antibodies may be obtained by using the multi-valent constructs described above as antigens. The resulting antibodies are capable of binding the selected HIV antigen as it appears in the biological fluids of an infected subject.

Additionally, the peptides of the present invention may also be used to generate antibodies that can be used as templates to generate anti-idiotype antibodies having the internal image of the neutralizing epitope structure contained in the peptide sequence. These antibodies, polyclonal or monoclonal, can then be used in vaccine formulations or in active immunotherapy. Accordingly, the present invention also includes monoclonal or polyclonal antibodies that carry the internal image of the peptides, as well as methods for generating these antibodies [PCT/US90/05393]. This published application is incorporated by reference herein, with particular reference to the discussion of antibodies therein.

Where it is desirable to obtain and utilize monoclonal antibodies (MAb) for the compositions and the methods of this invention, hybridoma cell lines expressing desirable MAbs may be generated by well-known conventional techniques, e.g. Kohler and Milstein, and using available tumor cell lines.

Recombinant antibodies may be generated using known techniques for their production [W. D. Huse et al, *Science*, 246:1275–1281 (1989)]. Desirable high-titer antibodies may also be generated by applying known recombinant techniques to the monoclonal or polyclonal antibodies developed to these antigens [see, e.g., PCT Patent Application No. PCT/GB85/00392; British Patent Application Publication No. GB2188638A; Amit et al., *Science*, 233:747–753 (1986); Queen et al., *Proc. Nat'l. Acad. Sci. USA*, 86:10029–10033 (1989); PCT Patent Application No. PCT/WO9007861; Riechmann et al., *Nature*, 332:323–327 (1988); and Barbas et al, *Proc. Natl. Acad. Sci. USA*, 89:4457–4461 (1992)].

These peptides, fragments and antibodies of this invention are thus useful as diagnostic reagents and vaccine components useful in the prophylaxis of HIV. The peptides and antibodies thereto may be associated with a diagnostic label, a chemical moiety, a toxin, another protein or peptide, provided that the peptide associated with such a molecule is characterized by substantially the same biological activity as the original peptide.

III. Identifying HIV Epitopes and Peptides

The present invention also provides a means for identifying additional HIV peptides and epitopes which correlate with predilection for vertical transmission. According to this method, the sites on the HIV-1 envelope to which maternal antibodies bind in biologic assays such as ELISA or radioimmunoassay (RIA) are mapped. As described in greater detail in Examples 3 and 4 below, a wide variety of gp160 envelope peptides within one or more selected HIV-1 isolate(s), e.g., MN strain, are screened by neutralizing antibodies from maternal sera from individuals with known maternally transmissible and non-transmissible HIV. This screen provides two sets of peptide recognition or binding data.

These screens provide peptides which are strongly recognized by neutralizing antibodies from individuals with maternally non-transmissible HIV. Maternally transmissible sera recognizes a smaller subset of the peptides used in the screen at detectably lower titer. The former set of recognized peptides have been shown to have some ability to predict protection from vertical transmission. Examples 3 and 4 demonstrate that women who did not transmit the virus had high titers of neutralizing antibodies to a collection of peptides of this invention, as assessed by a neutralization assay.

The performance of these screens also permitted the identification of certain of the peptides, e.g., SEQ ID NO: 6 in Example 3, to which the neutralizing antibodies bound. This peptide recognition clearly correlated to non-transmission status. For example, humoral antibody responses to several peptides from the gp41 envelope glycoprotein seemed to be mostly associated with protection of the fetus from vertical transmission, e.g., non-transmission status, although there was not a 100% association in this small sample group. More striking was the importance of a combinatorial humoral response, to peptides from both gp41 and gp120 (see Example 3, part C, below). Maternal reactive serum was more likely to be from a non-transmitting mother if antibodies were present to both the gp41 and gp120 envelope proteins rather than if there was a humoral response to only one peptide.

Several HIV peptides have been identified, particularly in those regions outside of the V3 loop of gp120, which appear to have a relationship to transmission status as well as to in vitro anti-HIV-I biological activity. For example, peptides (a) to (t) listed above, correlate well to lack of vertical transmission. These peptides are thus particularly desirable for inclusion in the panel of peptides which is useful for diagnostic purposes, discussed herein. These peptides are also anticipated to be useful in vaccinal compositions and in generating antibodies for use in therapeutic compositions, e.g. passive immunization.

Using the techniques described above, it is anticipated that one of skill in the art could identify other suitable peptides and epitopes. Identification of these peptides and epitopes implicated in non-transmission and maternal humoral immune responses which protect the fetus from vertical transmission permits the use of these peptides in vaccinal and therapeutic, as well as diagnostic methods.

IV. Diagnostic Method and Kit

The present invention provides a method for distinguishing between pregnancies in which there is a high or low rate of vertical transmission making use of the peptide collection of the invention. This method involves, generally, obtaining a sample from a subject known to have, or suspected of being infected with, HIV and screening the sample with a panel of peptides. Samples from individuals having an immune status consistent with low risk of vertical transmission respond to a larger number of peptides, e.g., at least two-fold more peptides, and exhibit a stronger immune response as reflected in higher titers of antibody, in comparison to samples from subjects at high risk of vertical transmission status.

Suitable samples include biological fluids and tissue. For purposes of this invention, the term biological fluids includes plasma, serum, whole blood, saliva, amniotic fluid, tears, urine and vaginal wash samples.

Alternatively, when used individually or in combinations smaller than the HIV panels discussed above, the HIV peptides, multivalent constructs, and/or antibodies of this invention may be useful for a variety of purposes. For example, selected peptides or multivalent constructs may be labeled with conventional diagnostic detectable labels and employed to detect the occurrence of anti-HIV antibodies in patient serum. Conversely, the antibodies of this invention may be employed to detect the occurrence of the naturally-occurring viral peptides in an infected patient's biological fluids. These peptides, constructs and antibodies are thus useful in diagnosis of HIV, particularly the diagnosis of a predilection for vertical transmission.

Utilizing the peptides and antibodies thereto which correlate with vertical transmission status as diagnostic reagents, HIV-infected patients can be readily identified as being at risk of vertically transmitting their infection. This information can be valuable in planning treatment for the infant as well as the mother. For example, the method of the invention can be used to predict whether or not the offspring of an HIV infected mother is itself infected, particularly prior to 24 months of age, by obtaining a suitable sample from either the mother or the infant. Testing of infants did not yield useful results under prior art methods because of the immaturity of the immune system in a newborn. Similarly, such diagnostic uses may be made in the general population, rather than simply in vertical transmission, if the antibodies implicated in vertical transmission are also implicated in horizontal transmission.

For use in diagnostic reagents and assays, the peptides, peptide constructs and antibodies of this invention may be associated with conventional labels which are capable, alone or in concert with other compositions or compounds, of providing a detectable signal. Where more than one antibody is employed in a diagnostic method, the labels are desirably interactive to produce a detectable signal. Most desirably, the label is detectable visually, e.g. colorimetrically. A variety of enzyme systems have been described in the art which will operate to reveal a colorimetric signal in an assay, e.g., glucose oxidase, peroxide, and tetramethyl benzidine (TMB) system, a horseradish peroxidase (HRP) system and similar enzyme systems. Other label systems that may be utilized in the methods of this invention are detectable by other means, e.g., colored latex microparticles [Bangs Laboratories, Indiana], fluorescent compounds, radioactive compounds or elements, or immunoelectrodes.

Detectable labels for attachment to the peptides, constructs and antibodies useful in diagnostic assays of this invention may be easily selected from among numerous compositions known and readily available to one skilled in the art of diagnostic assays. The diagnostic methods and peptides or antibodies of this invention are not limited by the particular detectable label or label system employed.

Various assay protocols may be employed for detecting the presence of naturally occurring antibodies capable of binding the HIV peptides associated with vertical transmission status identified herein or the naturally-occurring HIV peptide sequences as they occur in the biological fluids of HIV infected subjects. Of particular interest is the use of an isolated HIV peptide associated with vertical transmission status of this invention as a labeled reagent, optionally bound to an immobilizing agent, e.g., a well or plate, to determine whether antibody in the biological fluid sample will become bound to (form antigen-antibody complexes with) the identified peptide.

Assays employing an HIV peptide or peptide construct or antibody of the invention can be heterogenous (i.e., requiring a separation step) or homogenous. If the assay is heterogenous, a variety of separation means can be employed, including centrifugation, filtration, chromatography, or magnetism. One preferred assay for the screening of biological fluids is an enzyme linked immunosorbent assay, i.e., an ELISA.

Alternatively, an assay could be performed to determine the presence of the particular HIV peptide as it is naturally associated with the virus in the patient's sample. This assay involves incubating the sample, e.g. serum, with a labeled antibody of this invention such that specific binding occurs (antigen-antibody complex). Subsequently, excess labelled antibody is optionally removed, and the reaction mixture is analyzed to determine the presence or absence of the antigen-antibody complex and the amount of label associated with the antibody.

It should be understood by one of skill in the art that any number of conventional assay formats, particularly immunoassay formats, may be designed to utilize the HIV peptides, constructs therefor, and antibodies of this invention for the detection of HIV infection and the transmission status thereof in humans. This invention is thus not limited by the selection of the particular assay format, and is believed to encompass assay formats which are known to those of skill in the art.

For convenience, reagents for assays according to this invention may be provided in the form of kits. These kits can include microtiter plates to which the HIV peptides or constructs or antibodies of the invention have been preadsorbed, various diluents and buffers, labeled conjugates for the detection of specifically bound peptides or antibodies, and other signal-generating reagents, such as enzyme substrates, cofactors and chromogens. Other components of these kits can easily be determined by one of skill in the art. Such components may include polyclonal or monoclonal capture antibodies to the selected HIV peptide or a cocktail of two or more of the antibodies, a suitable standard including a purified or semi-purified HIV peptide standard, MAb detector antibodies, an anti-idiotypic antibody with indicator molecule conjugated thereto, an ELISA plate prepared for absorption, indicator charts for colorimetric comparisons, disposable gloves, decontaminations instructions, applicator sticks or containers, and a sample preparator cup. These kits provide a convenient, efficient way for a clinical laboratory to diagnose various HIV transmissible or non-transmissible infection.

V. Vaccinal Compositions and Immunization

As demonstrated by the results of the examples below, the lack of vertical transmission (referred to as non-transmission) correlates with high viral neutralization activity, but not with antisyncytial activity or binding to the V3 peptides examined. Also, the transmission group bound to fewer gp41 peptides when compared to the non-transmission group, further supporting the conclusion immune responses to gp41 are important in preventing transmission.

A. Active Immunization

Thus, the present invention also provides vaccine compositions useful for preventing transmission of HIV from a mother to her offspring. Such vaccine compositions contain an HIV peptide, fragment or analog of the invention correlating with either vertical transmission or lack of vertical transmission identified herein, combinations thereof or multivalent peptide constructs of the invention. Such a vaccine composition may contain the HIV peptide or construct according to the invention together with a pharmaceutically acceptable carrier or diluent suitable for administration as a composition for prophylactic treatment of HIV infections. Suitable pharmaceutically acceptable carriers facilitate administration of the proteins but are physiologically inert and/or nonharmful.

Carriers may be selected by one of skill in the art. Exemplary carriers include sterile saline, lactose, sucrose, calcium phosphate, gelatin, dextrin, agar, pectin, peanut oil, olive oil, sesame oil, and water. Additionally, the carrier or diluent may include a time delay material, such as glycerol monostearate or glycerol distearate alone or with a wax. In addition, slow release polymer formulations can be used.

This vaccine composition may contain one, or preferably more than one, non-transmissible HIV peptide, fragment and/or peptide constructs of the invention which is associated with non-transmission status. Such a vaccine may be useful in uninfected individuals to induce protective titers of neutralizing anti-HIV antibodies. In one embodiment, a vaccine composition may contain a 'cocktail' of multiple individual peptides (a) through (t) above, selected for their relationship to non-transmissible status. In another embodiment the cocktail may contain the other transmission-associated HIV peptides identified in Table 2 below. In still another embodiment multiple copies of a single HIV peptide of this invention, or multiple copies of more than one of these peptides may be employed in a single construct. For example, the peptides may be fused in frame to each other, or via a linker. Alternatively, multiple HIV peptides of this invention may be present in a multivalent peptide construct which contains multiple copies of one or more than one, of the peptides of this invention fused or linked to an inert carrier, to another protein, or to a lysine core.

An alternative, desirable vaccine composition may contain a conventional bio-expression vector, such as an adenovirus, poliovirus, vaccinia virus or retrovirus, into which the sequences of one or more of the HIV peptides or antibodies, or functional fragments thereof are inserted under the control of the viral expression regulatory sequences [see, e.g., U.S. Pat. No. 4,920,209]. Such viral vector compositions can be employed to deliver the relevant peptide or antibody sequences to the patient.

Optionally, the vaccine composition may further contain adjuvants, preservatives, chemical stabilizers, or other antigenic proteins. Typically, stabilizers, adjuvants, and preservatives are optimized to determine the best formulation for efficacy in the vaccinee. Suitable preservatives include chlorobutanol, potassium sorbate, sorbic acid, sulfur dioxide, propyl gallade, the parabens, ethyl vanillin, glycerin, phenol, parachlorophenol.

One or more of the above described vaccine components may be admixed or adsorbed with a conventional adjuvant. The adjuvant is used as a non-specific irritant to attract leukocytes or enhance an immune response. Such adjuvants include, among others, mineral oil and water, BCG, aluminum hydroxide, Avridine, L121/squalene, D-lactide-polylactide/glycoside, muramyl dipeptide, killed Bordetella, saponins, as Quil A.

Suitable amounts of the active ingredient can be determined by one of skill in the art based upon the level of immune response desired. In general, however, the vaccine composition contains between 1 ng to 1000 mg peptide and more preferably, 0.05 μg to 1 mg per mL, whether a single HIV peptide of the invention or a combination of these peptides or peptide constructs is employed. Antigens to other pathogens, such as measles, mumps, and rubella (MMR) vaccines, may be combined in a vaccine composition of the invention.

Suitable doses of the vaccine composition of the invention can be readily determined by one of skill in the art. Generally, a suitable dose is between 0.1 to 5 mL of the vaccine composition. Further, depending upon the patient being treated, i.e. weight, age, sex and general health, the dosage can also be determined readily by one of skill in the art.

The present invention also provides a prophylactic method entailing administering to a subject an effective amount of such a composition. For example, for prevention of vertical transmission, a vaccine composition of the invention could be administered either to a pregnant HIV-infected woman or an HIV-infected woman of child-bearing age. In general, the vaccine will be administered once, or preferably, more frequently depending on the likelihood of exposure to the virus. Where desirable, boosters may be administered. The vaccine may be administered by any suitable route. However, parenteral administration, particularly intramuscular, and subcutaneous, is the preferred route. Also preferred is the oral route of administration.

B. Passive Immunization

The present invention further provides pharmaceutical compositions useful in providing passive immunity against HIV. Such compositions are useful for administration to individuals anticipating risk of exposure to the HIV virus, e.g., prior to surgery or for health-care workers.

These compositions comprise one or more antibodies of the invention and a suitable carrier or diluent. These carriers, as well as suitable optional ingredients are as defined above with regard to vaccinal compositions for active immunization.

Additionally, this composition may further contain other active ingredients including, for example, AZT, DDC, DDI, biological response modifiers, such as interleukins, colony stimulating factors, especially GM-CSF, IFNs, and other immunostimulatory cytokines, as well as preservatives, or chemical stabilizers.

Suitable dosages can be determined by the attending physician, with reference to the discussion herein relating to appropriate doses for the therapeutic and vaccinal compositions of the invention. The composition administration may be by any appropriate route and repeated as necessary.

VI. Therapeutic Compositions The peptides identified herein as correlating with maternal non-transmission status can be used in active immunotherapy of HIV-positive individuals to initiate or boost their immune response of neutralizing antibodies.

Thus, the peptides, multivalent constructs and antibodies of this invention may also be used in therapeutic compositions for treating subjects who test positive for, or, prior to testing, exhibit symptoms of, AIDS or a related non-symptomatic condition. In one therapeutic embodiment, one or more antibodies of this invention, preferably directed to more than one of the non-transmission associated or the transmission associated peptides, may be used therapeutically as targeting agents to deliver virus-toxic or infected cell-toxic agents to HIV infected cells. Rather than being associated with labels for diagnostic uses, a therapeutic agent employs the antibody linked to an agent or ligand capable of disabling the replicating mechanism of the virus or of destroying the virally-infected cell. The identity of the toxic ligand does not limit the present invention. It is expected that preferred antibodies to the HIV peptides may be screened for the ability to internalize into the infected cell and deliver the ligand into the cell.

Such a therapeutic composition may be formulated to contain a carrier or diluent and one or more of the antibodies of the invention. Such carriers are discussed above in connection with vaccinal compositions.

Alternatively, or in addition to the antibodies of the invention, antagonists to the HIV peptides of the invention are expected to be useful in reducing and eliminating disease symptoms. It should be noted that the antibodies, peptides and constructs of this invention may be used for the design and synthesis of either peptide or non-peptide compounds (mimetics) which would be useful in the same therapy as the antibodies [See, e.g., Saragovi et al., *Science*, 253:792–795 (1991)]. The development of therapeutic compositions containing these agents is within the skill of one of skill in the art in view of the teaching of this invention.

Optionally, this composition may also contain other therapeutic agents useful in treating HIV infection, such as those discussed above in connection with compositions for passive immunization. Suitable non-therapeutic ingredients which may be used in a therapeutic composition in conjunction with the antibodies of the invention include, for example, casamino acids, sucrose, gelatin, and phenol red.

According to the method of the invention, a person may be treated for HIV infection by administering an effective amount of such a therapeutic composition. Preferably, such a composition is administered parenterally, preferably intramuscularly or subcutaneously. However, it may also be formulated to be administered by any other suitable route, including orally or topically.

A therapeutic composition of the invention may contain between about 0.05 µg/mL to about 1000 µg/mL of an antibody of the invention. Such a composition may be administered 1–3 times per day. However, suitable dosage adjustments may be made by the attending physician depending upon the age, sex, weight and general health of the patient.

The following examples illustrate the preferred methods for identification and selection of HIV peptides which correlate with lack of vertical transmission of HIV from mother to infant and which are thus useful in the diagnostic panels and/or vaccinal and therapeutic compositions of the invention. Examples 1–4 illustrate one experiment, which used fourteen peptides, spanning 46% (a total of 239 amino acids) of the gp120 external membrane glycoprotein and seventeen peptides spanning 66% (a total of 236 amino acids) of the gp41 transmembrane glycoprotein were used in binding assays of the maternal serum samples. Binding was examined by radioimmunoassay (RIA) or enzyme-linked immunosorbant assay (ELISA), as described in Example 3 below. A list of the gp120 and gp41 peptides tested, their location in the envelope glycoprotein and sequences are presented in Table 2 of Example 2. Example 5 provides another experiment using an expanded peptide panel. See Table 9. Example 6 provides yet another study using an expanded peptide panel and an expanded number of sera samples. See Table 12 and FIG. 1. These examples are illustrative only and do not limit the scope of the invention.

EXAMPLE 1

Origin and Classification of Patient Samples

The maternal sera and plasma samples were obtained through a collaborative investigation with the Mothers/Infants Cohort Study [J. Goedert et al, cited above]. Briefly, the Mothers/Infants Cohort Study is a prospective investigation and the sera samples in this study were from women attending obstetric clinics in New York City. All the women were drug abusers and/or Haitian. They were all established to be HIV seropositive by ELISA and Western blot analysis during the first trimester [Centers for Disease Control, "Interpretation and use of the Western blot assay for serodiagnosis of human immunodeficiency virus type 1 infections." *MMWR,* 38: S1–7 (1989); CDC, "Update: serological testing for antibody to human immunodeficiency virus." *MMWR,* 36:833–845 (1988)].

Sample number 13 was from a mother in the process of seroconverting late in the third trimester and this particular sample, although weakly reactive in enzyme linked immunosorbent assay against viral lysate and several peptides, was not unequivocally positive by standard whole virus Western blot.

In addition, information on the HIV infected status of the offspring of these women was also available. Seropositive mothers whose infants are found to meet the Centers for Disease Control (CDC) definition of perinatal HIV-1 infection are classified as transmitting mothers, whereas seropositive mothers of children with no sign of infection and who have lost maternal antibody are classified as non-transmitting mothers [CDC, "Classification system for human immunodeficiency virus (HIV) infection in children under 13 years of age." *MMWR,* 36:225–236 (1987)]. In this study, 13/20 of the mothers (65%) were classified as transmitters, whereas 7/20 of the mothers (35%) were classified as non-transmitters. Of the seven infected children, 2 had asymptomatic infection (CDC Classification P-1) while 5 had symptomatic infection (CDC Classification P-2). All of the maternal serum samples tested in this study were drawn during the last trimester of pregnancy. These patient samples were heat inactivated for 60 minutes at 56° C. before use in peptide binding or biological characterization assays of Examples 3 and 4.

EXAMPLE 2

Sources of Cell Lines and Peptides

The H9 cell line (a cutaneous T lymphoma line) infected by HIV-IIIB [ATCC CRL 8543] was used in the neutralization assay. The H9 cell line infected by HIV-MN was used in the anti-syncytial assays. SupT1 and Hut78 cells were used as the target cell lines for the anti-syncytial and neutralization assays. All cell lines were obtained from the National Institutes of Health AIDS Repository (Bethesda, Md.).

Synthetic peptides were developed according to methods described by C. Romano et al, *J. Neurochem.*, 53:362–369 (1989). The gp120 and gp41 peptides used in these assays are listed in Table 2 below. They were synthesized based on the sequence of the IIIB isolate of HIV-1. Each of the peptides was at least 80% pure, making them suitable for ELISA/RIA assays. The following peptides used in this study were generous gifts of Dr. Jay Berzofsky of the National Institute of Health: 35, 36, 40, 41, 93, 94, 95, 96, 97, 106, 107, 117, 120, 121, 123, 128, 129, and 132 [SEQ ID NOS: 5, 24, 25, 26, 10, 1, 11, 12, 13, 15, 16, 19, 21, 22, 23, 28, 29, and 30, respectively]. These sequences can be found in Human Retroviruses and AIDS, cited above.

TABLE 2

| | gp120 and gp41 Peptides Screened in Assay | | |
|---|---|---|---|
| Peptide Name | First Amino Acid | Last Amino Acid | Sequence |
| gp120 Peptides | | | |
| 60 | 031 | 052 | ATEKLWVTVYYGVPVWLEATTTL [SEQ ID NO: 9] |
| 93 | 051 | 065 | TLPCASDAKAYDTEV [SEQ ID NO: 10] |
| 94 | 061 | 075 | YDTEVHNVWATHACV [SEQ ID NO: 1] |
| 95 | 071 | 085 | THACVPTDPNPQEVV [SEQ ID NO: 11] |
| 96 | 081 | 095 | PQEVVLVNVTGENFNM [SEQ ID NO: 12] |
| 97 | 127 | 141 | VSLKCTDLKNDTNTN [SEQ ID NO: 13] |
| 59 | 145 | 165 | SSGRMIMEKGEIKNCSFNIST [SEQ ID NO: 14] |
| 106 | 296 | 310 | CTRPNNNTRKSIRIQ [SEQ ID NO: 15] |
| 107 | 303 | 317 | TRKSIRIQRGPGRAF [SEQ ID NO: 16] |
| 1029/33 | 304 | 314 | RKSIGIQRGPGR [SEQ ID NO: 2] |
| p18p | 308 | 322 | RIQRGPGRAFVTIGK [SEQ ID NO: 17] |
| B138 | 421 | 438 | KQFINMWQEVGKAMYAPP [SEQ ID NO: 3] |
| 466 | 468 | 483 | CFRPGGGDMRDNWREL [SEQ ID NO: 4] |
| 497 | 499 | 511 | CTKAKRRVVQREKA [SEQ ID NO: 18] |
| gp41 Peptides | | | |
| 117 | 515 | 529 | IGALFLGFGAAGST [SEQ ID NO: 19] |
| 560 | 548 | 577 | CIVQQQNNLLRAI-EAQQHLLQLTVWGIKQL [SEQ ID NO: 20] |
| 35 | 553 | 574 | QNNLLRAIEAQQHLLQLTVWGI [SEQ ID NO: 5] |
| 120 | 572 | 585 | WGIKQLQARILAVER [SEQ ID NO: 21] |
| 121 | 581 | 595 | LAVERYLKDQQLLGI [SEQ ID NO: 22] |
| 123 | 601 | 615 | KLICTTQVPWNASWS [SEQ ID NO: 23] |
| 36 | 612 | 626 | ASWSNKSLEQIWNNM [SEQ ID NO: 24] |
| 40 | 632 | 646 | DREINNYTSLIHSLI [SEQ ID NO: 25] |
| 41 | 637 | 651 | NYTSLIHSLIEESQNQ [SEQ ID NO: 26] |
| 649 | 649 | 662 | CQNQQEKNEQELLEL [SEQ ID NO: 6] |
| 53 | 662 | 682 | ELDKWASLWNWFNITNWLWY [SEQ ID NO: 7] |
| 55 | 696 | 716 | LRIVFAVLSVVNRVRQGYSP [SEQ ID NO: 27] |
| 128 | 711 | 725 | GYSPLSFQTHPIPR [SEQ ID NO: 28] |
| 129 | 736 | 750 | EGGERDRDRSIRLVN [SEQ ID NO: 29] |
| 132 | 766 | 780 | FSYHRLRDLLLIVTR |

TABLE 2-continued

| | gp120 and gp41 Peptides Screened in Assay | | |
|---|---|---|---|
| Peptide Name | First Amino Acid | Last Amino Acid | Sequence |
| 57 | 778 | 797 | [SEQ ID NO: 30]<br>VTRIVELLGRRGWEALKYWW |
| 1103/55 | 817 | 841 | [SEQ ID NO: 8]<br>NATAIAVAEGTDRVIEVVQGAYRAI<br>[SEQ ID NO: 31] |

EXAMPLE 3

RIA and ELISA Binding Assays

Radioimmunoassay (RIA) and enzyme-linked immunosorbent assay (ELISA) were performed by standard methodologies [E. Engvall, *Meth. Immunol.*, 70:419–439 (1980); S. K. Pierce et al, *J. Exp. Med.*, 144:1254–1262 (1976)]. Peptides were dissolved in 0.05M carbonate-bicarbonate buffer (pH 9.6) at a concentration of 10 µg/ml. Fifty µl (500 ng) of the peptides were immobilized in 96 well polyvinylchloride plates (Dynatech Laboratories, Inc.) overnight at 4° C. Plates were washed and non-specific sites were blocked with PBS containing 1% BSA overnight at 4° C.

Dilutions of HIV positive maternal sera were made in blocking buffer at dilutions of 1:50 and 1:500 and incubated in peptide coated plates overnight at 4° C. Plates were washed with PBS and incubated with 75,000 cpm of $^{125}$I-labelled goat anti-human IgG. The antibody was iodinated by a chloramine T method [W. V. Williams et al, *Proc. Natl. Acad. Sci. USA*, 85:6488–6492 (1988)]. Plates were washed, dried and counted in a gamma counter to measure specific binding. Normal human serum (i.e., HIV seronegative) was used as a control.

Alternatively, ELISA assays were performed in polystyrene plates (Dynatech Laboratories, Inc) in which 0.05% Tween 20 (Sigma Chemical Co.) was included in the washing, blocking and dilution buffers. The secondary antibody used was goat anti-mouse Ig conjugated to horseradish peroxidase (HRP) (Sigma Chemical Co). The substrate used for color development was 3,3',5,5' tetramethyl-benzidine dihydrochloride (TMB) (Sigma Chemical Co). Absorbance of samples was measured in a Dynatech MR5000 (Dynatech Laboratories, Inc.) plate reader and expressed as an optical density at wavelength of 450 nm ($OD_{450}$).

The results of the binding assays are represented in Tables 3, 4, 6 and 7. The following key is used for the designation of specific binding of the maternal sera samples to the peptides: The minus sign, –, is equivalent to the specific $OD_{450}$ or cpm of sera sample binding to peptide divided by the specific $OD_{450}$ or cpm of NHS sample binding to peptide, which value is less than 2. The plus sign, +, is equivalent to the specific $OD_{450}$ or cpm of sera sample binding to peptide divided by the specific $OD_{450}$ or cpm of NHS sample binding to peptide, which value is between 2 to 3. The double plus sign, ++, is equivalent to the specific $OD_{450}$ or cpm of sera sample binding to peptide divided by the specific $OD_{450}$ or cpm of NHS sample binding to peptide, which value is greater than 3.

Specific binding is defined as the difference between the $OD_{450}$ or cpm of sera to wells with peptide and the $OD_{450}$ or cpm of sera to wells without peptide.

Comparisons of number of peptides which bound maternal serum samples were made between the transmission group and the nontransmission group. The data was analyzed using the unpaired student's test. For the determination of differences in the binding of specific peptides between transmission and non-transmission groups, the Spearman's rank-order correlation test was performed.

A. Binding of Maternal Sera to gp 120 peptides

Tables 3 and 4 summarize binding data of the maternal sera samples to the peptides from gp 120.

TABLE 3

Screening of Maternal HIV+ Sera Against Peptides
From gp120
Sera No. - Non-Transmission Group

| Peptide | 1 | 2 | 3 | 6 | 7 | 8 | 9 | 11 | 12 | 16 | 17 | 18 | 20 |
|---|---|---|---|---|---|---|---|---|---|---|---|---|---|
| 60<br>[SEQ ID NO: 9] | – | – | – | – | – | – | – | – | – | – | – | – | – |
| 93<br>[SEQ ID NO: 10] | ++ | – | – | + | ++ | + | – | – | – | + | – | – | – |
| 94<br>[SEQ ID NO: 1] | ++ | – | ++ | – | – | – | – | – | – | – | – | – | – |
| 95<br>[SEQ ID NO: 11] | + | – | – | – | – | – | + | – | – | – | – | – | – |
| 96<br>[SEQ ID NO: 12] | – | – | – | – | – | – | – | – | – | – | – | – | – |
| 97<br>[SEQ ID NO. 13] | – | – | – | – | – | – | – | – | – | – | – | – | – |
| 59<br>[SEQ ID NO: 14] | – | – | – | – | – | – | – | – | – | – | – | – | – |
| 106<br>[SEQ ID NO: 15] | – | – | – | – | – | – | – | – | + | ++ | – | + | |
| 107 | ++ | ++ | ++ | ++ | + | ++ | ++ | ++ | ++ | ++ | ++ | ++ | ++ |

TABLE 3-continued

Screening of Maternal HIV+ Sera Against Peptides
From gp120
Sera No. - Non-Transmission Group

| Peptide | 1 | 2 | 3 | 6 | 7 | 8 | 9 | 11 | 12 | 16 | 17 | 18 | 20 |
|---|---|---|---|---|---|---|---|---|---|---|---|---|---|
| [SEQ ID NO: 16) 1029-33 | + | ++ | + | – | – | – | – | + | + | – | + | – | ++ |
| [SEQ ID NO: 2] p18p | – | – | – | – | – | – | – | – | ++ | + | ++ | – | + |
| [SEQ ID NO: 17] B138 | + | + | – | + | ++ | ++ | – | – | – | – | – | – | – |
| [SEQ ID NO: 3] 466 | – | – | – | + | – | – | ++ | – | – | – | + | – |   |
| [SEQ ID NO: 4] 497 | – | ++ | ++ | + | – | ++ | ++ | ++ | – | ++ | ++ | + | + |
| [SEQ ID NO: 18] |   |   |   |   |   |   |   |   |   |   |   |   |   |

TABLE 4

Screening of Maternal HIV+ Sera Against Peptides
From gp120
Sera No. - Transmission Group

| Peptide | 4 | 5 | 10 | 13 | 14 | 15 | 19 |
|---|---|---|---|---|---|---|---|
| 60 [SEQ ID NO: 9] | – | – | – | – | – | – | – |
| 93 [SEQ ID NO: 10] | ++ | – | – | – | – | – | – |
| 94 [SEQ ID NO: 1] | – | – | – | – | – | – | – |
| 95 [SEQ ID NO: 11] | – | – | – | – | ++ | – | – |
| 96 [SEQ ID NO: 12] | – | – | – | – | – | – | – |
| 97 [SEQ ID NO: 13] | – | – | – | – | – | – | – |
| 59 [SEQ ID NO: 14] | – | – | – | – | – | – | – |
| 106 [SEQ ID NO: 15] | – | – | – | ++ | ++ | ++ | – |
| 107 [SEQ ID NO: 16] | ++ | ++ | + | ++ | ++ | – | ++ |
| 1029-33 [SEQ ID NO: 2] | – | + | – | + | – | + | – |
| p18p [SEQ ID NO: 17] | – | – | – | ++ | ++ | ++ | – |
| B138 [SEQ ID NO: 3] | + | + | – | – | – | – | – |
| 466 [SEQ ID NO: 4) | – | – | – | – | – | – | – |
| 497 [SEQ ID NO: 18] | ++ | + | + | – | – | ++ | + | i. Peptides from gp120 amino terminus

Several maternal serum samples had reactivity to one or more of three peptides spanning amino acid 51 through 85 of the amino terminus of gp120 HIV strain IIIB (peptides 93, 94 and 95 [SEQ ID NOS: 10, 1, and 11, respectively], Tables 2 and 3). No binding of maternal sera to four peptides from the amino terminus of HIV strain IIIB (peptides 59, 60, 96 and 97 [SEQ ID NOS: 14, 9, 12, and 13, respectively], Tables 2 and 3) was observed. Peptides 96 and 97 [SEQ ID NOS: 12 and 13, respectively] are from a region near to the putative sites for the binding of gp120 to gp41 of HIV strain IIIB; and deletion of the amino acid residues within this region of gp120 inhibits viral receptor binding of the CD4 molecule [D. P. Bolognesi, AIDS, 3:S111–S118 (1989)].

Of the six maternal sera binding to peptide 93 [SEQ ID NO: 10], 1(17%) was from the vertical transmission group and 5(83%) were from the non-transmission group. In addition, 3(50%) and 6(100%) of the six samples which bound possessed neutralization and anti-syncytial activity, respectively. Of the two maternal sera binding to peptide 94 [SEQ ID NO: 1], neither were from the vertical transmission group. Of the three maternal sera binding to peptide 95 [SEQ ID NO: 11], one was from the vertical transmission group.

ii. Peptides from the V3 loop of gp120

There was significant binding of a number of the maternal serum samples to peptides from the V3 loop of gp120 (HIV strain IIIB). The peptides 106, 107, 1029-33 and p18p [SEQ ID NOS: 15, 16, 2, and 17, respectively] span amino acids 296–322 and 30%, 95%, 50% and 35% of the maternal serum samples bound to these peptides respectively. See Table 5 below, in which values are the percentages of sera samples from each group demonstrating binding to peptide.

TABLE 5

|  | Peptides | | | |
|---|---|---|---|---|
| Transmission Status [SEQ ID NOS: | 106 15 | 107 16 | 1029–33 2 | p18p 17] |
| Transmitter n = 7 | 42.9 | 85.7 | 42.9 | 42.8 |
| Non-Transmitter n = 13 | 23.0 | 100 | 53.8 | 30.7 |

The data presented herein do not support the observation in the prior art [see, e.g., Rossi et al, Goedert et al, and Devash et al, cited above] of an association between binding to V3 and protection from vertical transmission. One potential reason for this discrepancy was the use of different V3 peptides in this example compared with those where an association was found. Neutralizing epitopes other than V3 epitopes could be involved or conformational epitopes (which may or may not involve anti-V3 responses) and may collectively mediate protection from vertical transmission.

The observation of neutralizing activity in one transmitting mother does not necessarily diminish the importance of this observation. Minor trauma or cell spread with or without trauma across the placenta may account for such transmission in the presence of neutralizing levels of antibodies.

iii. Peptides from the CD4 binding site.

Peptide B138 [SEQ ID NO: 3] spans amino acid 421 through 438 of HIV IIIB. Seven of the maternal samples reacted to peptide B138 [SEQ ID NO: 3], in contrast to prior observations that this region has appeared to be immunosilent in HIV infected patients. Of those samples which bound, two were from the vertical transmission group.

iv. Peptides from the carboxy terminus.

Sixteen (80%) of the maternal sera samples bound to peptide 497 [SEQ ID NO: 18] which spans amino acid 499–511 of the carboxy terminus of gp120 of HIV IIIB.

Seventy-seven and 71% of the samples from the transmission and non-transmission groups, respectively, bound to this peptide. This region is immunoactive but antisera generated to this peptide do not demonstrate neutralizing activity.

In addition, 15% of the maternal serum samples demonstrated reactivity to peptide 466 [SEQ ID NO: 4], which spans amino acid 468 through 483 of gp120. Zero and three of the maternal samples from the transmission and non-transmission groups, respectively, bound to this peptide. Of the three maternal samples which bound to peptide 466 [SEQ ID NO: 4], all of them demonstrated neutralizing and anti-syncytial activity. Antisera generated in animals against this peptide have been demonstrated to exhibit neutralizing activity [K. E. Ugen et al, "Inhibition of HIV-1 Cellular Infection by Immunologic Reagents", Vaccines 91. Modern Approaches to New Vaccines Including Prevention of AIDS., R. M. Chanock et al, (eds), Cold Spring Harbor Laboratory Press, pp. 115–121 (1991)]. In particular, one maternal serum (No.9) demonstrated very strong binding to peptide 466 [SEQ ID NO: 4] and also demonstrated high neutralizing and anti-syncytial activity. It is not clear whether this activity is due to binding to peptide 466 [SEQ ID NO: 4].

B. Binding of Maternal Sera to Peptides from gp41

Tables 6 and 7 summarize binding data to the peptides from gp41.

TABLE 7

Screening of Maternal HIV+ Sera Against Peptides From gp41
Sera No. - Transmission Group

| Peptide | 4 | 5 | 10 | 13 | 14 | 15 | 19 |
|---|---|---|---|---|---|---|---|
| 117 [SEQ ID NO: 19] | − | − | − | − | − | − | − |
| 560 [SEQ ID NO: 20] | − | − | − | − | − | − | − |
| 35 [SEQ ID NO: 5] | − | − | − | − | − | − | − |
| 120 [SEQ ID NO: 21] | − | − | − | − | − | − | − |
| 121 [SEQ ID NO: 22] | − | − | − | − | ++ | ++ | − |
| 123 [SEQ ID NO: 23] | − | − | − | − | − | − | − |
| 36 [SEQ ID NO: 24] | − | − | − | − | − | − | − |
| 40 [SEQ ID NO: 25] | − | − | − | − | − | − | − |
| 41 [SEQ ID NO: 26] | − | − | − | − | − | − | − |
| 649 [SEQ ID NO: 6] | + | − | − | − | + | + | − |
| 53 [SEQ ID NO: 7] | − | − | − | − | − | − | − |
| 55 | − | − | − | − | − | − | − |

TABLE 6

Screening of Maternal HIV+ Sera Against Peptides From gp41
Sera No.- Non-Transmission Group

| Peptide | 1 | 2 | 3 | 6 | 7 | 8 | 9 | 11 | 12 | 16 | 17 | 18 | 20 |
|---|---|---|---|---|---|---|---|---|---|---|---|---|---|
| 117 [SEQ ID NO: 19] | − | − | − | − | − | − | − | − | − | − | − | − | − |
| 560 [SEQ ID NO: 20] | + | − | − | − | − | − | − | − | − | − | − | − | − |
| 35 [SEQ ID NO: 5] | − | − | + | − | + | − | − | − | − | − | − | − | − |
| 120 [SEQ ID NO: 21] | − | − | − | − | − | − | − | − | − | − | − | − | − |
| 121 [SEQ ID NO: 22] | ++ | − | − | ++ | − | − | − | − | − | ++ | ++ | ++ | − |
| 123 [SEQ ID NO: 23] | + | − | − | − | − | − | − | − | − | − | − | − | − |
| 36 [SEQ ID NO: 24] | − | − | − | − | − | − | − | − | − | − | − | − | − |
| 40 [SEQ ID NO: 25] | − | − | − | − | − | − | − | − | − | − | − | − | − |
| 41 [SEQ ID NO: 26] | − | − | − | − | − | − | − | − | − | − | − | − | − |
| 649 [SEQ ID NO: 6] | ++ | + | + | ++ | ++ | ++ | − | ++ | ++ | − | + | + | − |
| 53 [SEQ ID NO: 7] | − | − | − | − | ++ | − | − | − | − | − | + | − | − |
| 55 [SEQ ID NO: 27] | − | − | − | − | − | − | − | − | − | − | − | − | − |
| 128 [SEQ ID NO: 28] | − | − | − | − | − | − | − | − | − | − | − | − | − |
| 129 [SEQ ID NO: 29] | + | − | − | − | − | − | − | − | − | − | − | − | − |
| 132 [SEQ ID NO: 30] | + | − | − | − | − | + | − | − | − | − | − | − | − |
| 57 [SEQ ID NO: 8] | − | − | − | − | − | ++ | − | − | − | − | − | − | + |
| 1105-55 [SEQ ID NO: 31] | − | ++ | − | ++ | ++ | ++ | − | − | ++ | − | ++ | ++ | − |

TABLE 7-continued

Screening of Maternal HIV+ Sera Against Peptides
From gp41
Sera No. - Transmission Group

| Peptide | 4 | 5 | 10 | 13 | 14 | 15 | 19 |
|---|---|---|---|---|---|---|---|
| [SEQ ID NO: 27] 128 | – | – | – | – | – | – | – |
| [SEQ ID NO: 28] 129 | – | – | – | – | – | – | – |
| [SEQ ID NO: 29] 132 | – | – | – | – | – | – | – |
| [SEQ ID NO: 30] 57 | – | – | – | – | – | – | – |
| [SEQ ID NO: 8] 1105-55 | ++ | – | – | – | ++ | – | – |
| [SEQ ID NO: 31] | | | | | | | |

In examining the binding of the maternal sera to peptides from gp41, it is evident that major reactivities to three peptides occur. Peptides 121 [SEQ ID NO: 22] (amino acid 581–595), 649 [SEQ ID NO: 6] (amino acid 649–663) and 1103/55 [SEQ ID NO: 31] (amino acid 817–841) demonstrated binding of 35%, 70% and 45% of the maternal sera samples, respectively. Spearman rank-order correlation coefficient analysis of the binding data indicates that there is a significant statistical difference in binding of samples from the transmission group to peptide 649 [SEQ ID NO: 6], compared to the non-transmission group, suggesting that binding to this peptide is correlated with non-transmission status.

C. Comparison of Binding to gp120 and gp41

Quantitative analysis of binding to the peptides is as follows:

Of the 13 maternal sera samples from the non-transmission group, 100% demonstrated binding to at least one peptide of both the gp41 and gp120 peptide groups. In contrast, of the 7 maternal samples from the transmission group, 100% demonstrated binding to at least one of the gp120 peptides; but only 43% (3 samples) bound to at least one of the gp41 peptides. On average, sera from the non-transmission group bound to approximately 33% more peptides than the samples from the transmission group.

There appears to be quantitative (number of peptides bound) differences in binding to gp41 and gp120 between the transmission and nontransmission groups. The following relationships can be determined, with average number expressed as the mean±standard error of the mean:

The seven transmission group sera samples bound to an average of 1.1±0.45 (or 24%) gp41 peptides and an average of 3.4±0.37 (or 76 %) gp120 peptides, for a total of 4.5±0.75.

Conversely, the thirteen non-transmission group sera samples bound to an average of 2.4±0.40 (or 36%) gp41 peptides and to an average of 4.2±0.35 (or 64%) gp120 peptides, for a total of 6.6±0.57. Statistically, there was a significantly higher average number of gp41 and combined (gp41+gp120) peptides to which the sera from the non-transmission group bound compared to the transmission group, i.e., p<0.05 by the unpaired Student's t-test. These data suggest that immune responses directed against gp41 are involved in protection of the fetus from infection by HIV-1.

EXAMPLE 4

Anti-Syncytial and Neutralization Assays

To analyze the effect of the maternal serum samples on HIV-1 fusion, SupT1 cells were used as target cells in an anti-syncytial assay. Dilutions of the different maternal serum samples were made in 96 well plates in RPMI 1640 media containing 10% fetal calf serum at final dilutions of 1:4, 1:8, 1:16, 1:32, 1:64, 1:128, 1:256 or 1:512. HIV-1 infected cells (MN isolate) were then plated in the wells at a density of approximately $10^4$ cells per well. SupT1 target cells were then added at $5\times10^5$/well and the number of syncytia are determined after 3 days of incubation. Inhibition of syncytium formation by a serum sample was considered significant if the dilution which yielded a 50% reduction in the number of syncytia when compared to control was greater than 1:32. The average number of syncytia in the control (normal human serum) wells at the above dilutions were: 45.5, 48.5, 44, 48, 48.5, 41.5, 42 and 45.5 respectively.

In a neutralization assay, 20 μl of maternal sera samples was placed in 96 round bottom well plates at final dilutions of 1:10, 1:90 and 1:810 in RPMI. The HIV-IIIB viral isolate was diluted in RPMI to a $TCID_{50}$ of 100 units/ml. Twenty μl of the virus solution was placed in each well and the plate was incubated for one hour at 4° C. Hut-78 cells were incubated with 2 μg/ml of polybrene for one hour at 37° C. in a $CO_2$ incubator. The HUT-78 cells were washed and resuspended in fresh RPMI to a final concentration of $4\times10^6$ cells/ml. Ten μl of the cell suspension was added to each well and the plate was incubated for one hour in a 37° C., $CO_2$ incubator.

Fifteen μl of the serum/cell/virus solution was aliquoted to a new plate containing 200 μl of fresh RPMI and incubated for 6 days. After 6 days, 100 μl was used to analyze for p24 antigen. The p24 capture ELISA assay kit (Coulter Corporation, Hialeah, Fla.) was used to perform the measurements.

Further, sera samples at the same dilutions as described above were tested for residual p24 core protein or antibody to insure the results were due only to viral infection. All samples failed to demonstrate residual p24 antigen or anti-p24 antibody at the above dilutions when tested in the p24 ELISA assay kit.

Table 8 summarizes data on anti-syncytial and neutralization activity for each of the maternal serum samples. In addition, these data are shown in relationship to gp41 and gp120 binding reactivities for each of the sera samples.

TABLE 8

Summary of Anti-Syncytial, Neutralization and Peptide
Binding Reactivities of Maternal Sera Samples

| Maternal Sera Samples Dilution | Anti-Syncytial Activity Dilution Resulting in ≧50% Inhibition[a] | Neutralization Activity Resulting in ≧50% Inhibition[b] | Peptide Binding Reactivity Number of gp41 Peptides Bound (+ or ++) | Number of gp120 Peptides Bound (+/++) |
|---|---|---|---|---|
| Non-Transmission Group | | | | |
| 1 | 1:64 | — | 6 | 6 |
| 2 | 1:32 | — | 2 | 4 |
| 3 | 1:256 | 1:90 | 2 | 4 |
| 6 | 1:512 | 1:90 | 3 | 5 |
| 7 | 1:64 | 1:810 | 3 | 3 |
| 8 | 1:128 | — | 4 | 4 |
| 9 | 1:256 | 1:810 | 1 | 3 |
| 11 | 1:256 | 1:810 | 1 | 4 |
| 12 | 1:512 | 1:90 | 2 | 3 |
| 16 | 1:512 | 1:810 | 1 | 5 |

TABLE 8-continued

Summary of Anti-Syncytial, Neutralization and Peptide Binding Reactivities of Maternal Sera Samples

| Maternal Sera Samples Dilution | Anti-Syncytial Activity Dilution Resulting in ≧50% Inhibition[a] | Neutralization Activity Dilution Resulting in ≧50% Inhibition[b] | Peptide Binding Reactivity | |
|---|---|---|---|---|
| | | | Number of gp41 Peptides Bound (+ or ++) | Number of gp120 Peptides Bound (+/++) |
| 17 | 1:256 | 1:810 | 4 | 5 |
| 18 | 1:64 | 1:810 | 3 | 3 |
| 20 | 1:256 | 1:10 | 1 | 5 |
| Transmission Group | | | | |
| 4 | 1:256 | 1:10 | 2 | 4 |
| 5 | 1:128 | — | 0 | 4 |
| 10 | 1:256 | — | 0 | 2 |
| 13 | 1:128 | 1:10 | 0 | 4 |
| 14 | 1:128 | 1:10 | 3 | 4 |
| 15 | 1:256 | 1:810 | 2 | 4 |
| 19 | 1:256 | 1:10 | 0 | 2 |

[a]Values are the lowest dilution of maternal sera which results in at least 50% decrease in the number of syncytia formed per well when compared to normal human serum.
[b]Values are the lowest dilution of maternal sera which results in at least 50% decrease in absorbance OD450 nm (a measure of p24 antigen levels), when compared to normal human serum.
(−) indicates negative (i.e. a dilution of <1:10)

There appears to be no correlation between anti-syncytial activity of the maternal serum samples and vertical transmission and non-transmission of HIV-1 infection. By the definition established for anti-syncytial activity (titer>1:32), all maternal sera samples except No. 2 possessed significant anti-syncytial activity. These data suggest that anti-syncytial assays are not a useful means for identifying mothers who do not transmit HIV-1 infection to their offspring.

Neutralizing activity by a serum sample was considered significant if the dilution which yielded a 50% reduction in $OD_{450}$ (a measure of p24 antigen levels) when compared to control was greater than 1:10 (i.e. in this assay dilutions of 1:0.90 or 1:810). According to this definition established for neutralizing ability, 9/13 (69.2%) of non-transmitting mothers exhibited significant neutralizing activity. In contrast, 1/7 (14.3%) of transmitting mothers possessed significant neutralizing activity.

Absent unusual bias in the sample population, this observation has direct importance for understanding the role of anti-HIV envelope humoral immune responses in preventing vertical transmission. These data indicate a relationship between high neutralization titers of maternal sera and non-transmission status.

EXAMPLE 5

Screening of Maternal Sera with Alternate Peptide Collection
A. Peptide Collection The gp120 and gp41 peptides used in this experiment include peptides 60 [SEQ ID NO:9], 93 [SEQ ID NO:10], 94 [SEQ ID NO:1], 95 [SEQ ID NO:11], 96 [SEQ ID NO:12], 97 [SEQ ID NO:13], 59 [SEQ ID NO:14], 106 [SEQ ID NO:15], 107 [SEQ ID NO:17], 1029/33 [SEQ ID NO:2], p18p [SEQ ID NO:17], B138 [SEQ ID NO:3], 466 [SEQ ID NO:4], 497 [SEQ ID NO:18], 117 [SEQ ID NO:19], F560 [SEQ ID NO:20], 35 [SEQ ID NO:5], 120 [SEQ ID NO:21], 121 [SEQ ID NO:22], 123 [SEQ ID NO:23], 36 [SEQ ID NO:24], 40 [SEQ ID NO:25], 41 [SEQ ID NO:26], 649 [SEQ ID NO:6], 53 [SEQ ID NO:7], 55 [SEQ ID NO:27], 128 [SEQ ID NO:28], 129 [SEQ ID NO:29], 132 [SEQ ID NO:30], 57 [SEQ ID NO:8], and 1103/55 [SEQ ID NO:31] from Table 2. The remainder of the peptides used in the study are provided in the following Table 9. These peptides were synthesized based on the same HIV IIIB isolate as were the peptides of Table 2. Alternative designations for these peptides are provided in brackets.

TABLE 9

| Peptide Name | Amino acids | Sequences |
|---|---|---|
| gp120 peptides | | |
| HP1 [1] | 93–107 | SEQ ID NO:99 |
| HP2 [2] | 98–112 | SEQ ID NO:100 |
| HP3 [3] | 102–116 | SEQ ID NO:101 |
| HP5 [5] | 105–117 | SEQ ID NO:102 |
| HP7 [7] | 107–121 | SEQ ID NO:103 |
| HP9 [9] | 141–155 | SEQ ID NO:104 |
| HP10 [10] | 157–171 | SEQ ID NO:105 |
| 99 | 181–195 | SEQ ID NO:106 |
| 101 | 201–215 | SEQ ID NO:107 |
| A69-39 [A6939] | 210–227 | SEQ ID NO:108 |
| 103 | 221–235 | SEQ ID NO:109 |
| PO61 | 248–269 | SEQ ID NO:110 |
| 17 | 267–282 | SEQ ID NO:111 |
| 105 | 286–300 | SEQ ID NO:112 |
| 1029/43 | 304–312 | SEQ ID NO:113 |
| BS-1 [BS1] | 319–329 | SEQ ID NO:114 |
| WSK-1 | 378–394 | SEQ ID NO:115 |
| DW-1 | 414–430 | SEQ ID NO:116 |
| DW-2 | 421–439 | SEQ ID NO:117 |
| DW-3 | 436–454 | SEQ ID NO:118 |
| gp41 peptides | | |
| 118 | 528–542 | SEQ ID NO:119 |
| ABT 581 | 576–592 | SEQ ID NO:120 |
| CRB 41-2 [Pep 2] | 593–604 | SEQ ID NO:121 |
| BS-1 | 625–634 | SEQ ID NO:122 |
| 124 | 646–660 | SEQ ID NO:123 |
| PO56 | 749–769 | SEQ ID NO:124 |
| PO58 | 795–818 | SEQ ID NO:125 |
| ABT 846 | 846–860 | SEQ ID NO:126 |

Each of the peptides was at least 85% pure, making them suitable for ELISA analyses. The average length of these peptides was 18 amino acid residues, which allows for a certain degree of local flexibility and conformational folding, thus facilitating detection of antibody species with reactivities to shaped structures.

B. Patient Samples

The maternal serum samples were obtained from the Mothers/Infants Cohort Study described in Example 1. For the ELISA peptide-binding analyses performed essentially as described in Example 3, maternal serum samples were diluted to 1:50 or 1:500 with blocking buffer (1% bovine serum albumin in phosphate-buffered saline containing 0.05% Tween 20). Binding was measured using 10 μg/mL peptide per well and was considered positive if the experimental/control $OD_{450nm}$ ratio was ≧2. Normal (HIV seronegative) human sera were used as controls.

C. Results

FIGS. 2A–2D depict the results of analysis of the gp120 peptide reactivities determined for this serum panel. Displayed is the percentage of serum samples from the transmission and non-transmission groups that binds to the V3 loop, CD4-binding site, and carboxyl and amino termini of gp120. No difference was observed between the two groups among the five different V3 peptides tested in this study.

Also examined was the binding to the putative CD4-binding region of gp120. No significant differences were observed in binding to any of these peptides between the two studied groups. Two epitopes from the carboxy-terminal region of gp120 have been examined. High reactivity but no difference between the two groups was observed in the binding of the panel to peptide 497, a peptide that can assume a type-2 β conformation and is located at the very terminal region of gp120. In contrast, the immune response of this panel to peptide 466 may have importance. For example, 3 of 13 non-transmission sera reacted with this peptide. All 3 of these sera exhibited neutralizing activity and possessed, to varying degrees, antisyncytial activity as well. With regard to peptide 466, it has been demonstrated that this peptide can elicit both antisyncytial and neutralizing activities. Differences in binding between the transmission and non-transmission groups are noted with peptides 93 and 95 in the amino terminus of gp120.

The reactivity to peptides derived from gp41 has also been examined. In general, ten peptides were recognized by the non-transmission group but were not recognized by the transmission group. However, six of the peptides were recognized by both groups. These included an immunodominant region peptide designated 41-2 (SEQ ID NO: 121) to which 90% of both groups bound and a peptide from the carboxyl region of gp41 designated 56 (SEQ ID NO: 124) to which more than 50% of both groups bound.

Table 10 below summarizes the reactivity of sera from the transmission and non-transmission groups that bind to all the peptides examined. Importantly, there are clear differences in peptide reactivity between the two groups. The difference was particularly apparent in analysis of reactivity to gp41. The transmission group reacted with 2.5±0.4 peptides, whereas the non-transmission group reacted with 3.9±0.5 peptides. Virtually all samples reacted with the immunodominant peptide from gp41, peptide 41-2. Therefore, if this peptide is removed from both groups, the difference in reactivity changes to 1.5 and 2.9 reactive peptides in the transmission and non-transmission groups, respectively. By this analysis, virtually twice the peptide reactivity is observed in the non-transmission group. In addition, overall reactivity to gp41 was also decidedly different. Only 6 of the peptides from gp41 were recognized by the transmission group (peptides 56, 58, 1103.55, 121, 41-2, and 649), whereas 16 peptides, including all of the 6 above, were recognized by some individuals in the non-transmission group.

TABLE 10

Average Number of gp120 and gp41 Peptides that Maternal Serum Samples Bind

| | Average ± standard error | | |
|---|---|---|---|
| | gp120 | gp41 | total (gp120 + gp41) |
| Transmission group = 7 | 4.7 ± 0.4 | 2.5 ± 0.4 | 7.2 ± 0.8 |
| Non-transmission group = 13 | 5.8 ± 0.4 | 3.9 ± 0.5 | 9.7 ± 0.9 |
| Percent decrease in binding of transmission vs. non-transmission group | 19 | 36 | 26 |

Analysis of the relationship between neutralization and antisyncytial activity was also examined (See Table 11 below). Neutralization activity correlated exceptionally well with non-transmission status. Retrospectively, a mother was less likely to transmit infection prenatally if her serum contained neutralizing activity than if her serum had no neutralizing activity. Surprisingly, there was no correlation between antisyncytial activity and transmission status.

TABLE 11

Relationship Between Vertical Transmission/Non-transmission Status and Antisyncytial and Neutralizing Activity of Maternal Sera

| Transmission status (total no. of samples = 20) | Neutralization (no. [%] exhibiting neutralizing activity) | Antisyncytial activity(no. [%] exhibiting antisyncytial activity) |
|---|---|---|
| Transmission group = 7 | 1 (14.3%) | 4 (57.1%) |
| Non-transmission group = 13 | 8 (61.5%) | 5 (38.5%) |

EXAMPLE 6

Screening of Maternal Sera with Peptide Collection

This study analyzes the binding of a larger population of maternal sera from vertical transmitter and non-transmitter mothers to a larger library of peptides from the envelope glycoprotein of HIV-1 than illustrated in the previous examples.

A. Patient Sera Samples

A total of 86 maternal sera samples obtained from patients of the Hospital of the University of Pennsylvania during the third trimester of pregnancy were used in this study 58 (67%) were non-transmitters and 28 (33%) were transmitters. This is approximately consistent with the national average (i.e. a rate of transmission between 25–30%). Transmission status was based upon serological or molecular diagnosis of children (at an age of greater than 15 months) born to these mothers. Because of the constraints on the volume of serum available for many of these samples, not all sera were analyzed with all the peptides. However, each sera sample was run with at least 40 peptides.

B. Peptide Reagents and Analysis

The peptides used in this study are among those shown topographically in FIG. 1. The location and sequences of these peptides are provided in Table 1, Table 2, Table 9, and in the following Table 12.

These peptides are of an average length of 16 amino acids and covered the entire external as well as the transmembrane glycoprotein of HIV-1. Peptide binding was analyzed by ELISA essentially as described in Example 3.

C. Results

The results of one study, using some of the peptides identified above among others, is provided in Table 12, which illustrates the number and percent of non-transmitters which bound to the tested peptide. The percentage designation refers to the percentage of sera samples which bound to a particular peptide. A value of greater than 0% means that at least one of the samples bound to the particular peptides.

TABLE 12

| Peptide | Sequence ID No. | N = 12 Non-Transmitters | N = 4 Transmitters |
|---|---|---|---|
| 53 | 7 | 0 (0%) | 0 (0%) |
| WSK-1 | 115 | 0 (0%) | 0 (0%) |
| 41-22 | 155 | 0 (0%) | 0 (0%) |
| DC419 (IIIB) | 191 | 0 (0%) | 0 (0%) |
| A6939 | 108 | 0 (0%) | 0 (0%) |
| (2) C21E | 147 | 0 (0%) | 0 (0%) |
| A110 (IIIB) | 192 | 0 (0%) | 0 (0%) |

TABLE 12-continued

| Peptide | Sequence ID No. | N = 12 Non-Transmitters | N = 4 Transmitters |
|---|---|---|---|
| 56 | 156 | 0 (0%) | 0 (0%) |
| 129 | 29 | 0 (0%) | 0 (0%) |
| BS-2 | 176 | 0 (0%) | 0 (0%) |
| 497 | 18 | 0 (0%) | 0 (0%) |
| 1029-33 | 2 | 0 (0%) | 0 (0%) |
| 1103-55 | 31 | 0 (0%) | 0 (0%) |
| 124 | 123 | 0 (0%) | 0 (0%) |
| C19Q | 137 | 4 (33.3%) | 0 (0%) |
| RG-1 | 177 | 3 (25%) | 1 (25%) |
| A524 | 163 | 0 (0%) | 0 (0%) |
| A620 | 172 | 1 (8.3%) | 0 (0%) |
| A824 | 175 | 0 (0%) | 0 (0%) |
| AIDS-PND | 134 | 7 (58.3%) | 1 (25%) |
| 649 | 6 | 7 (43.8%) | 2 (50%) |
| 40 | 25 | 1 (8.3%) | 0 (0%) |
| 58 | 173 | 3 (25%) | 0 (0%) |
| p18p | 17 | 3 (25%) | 0 (0%) |
| 41 | 26 | 0 (0%) | 0 (0%) |
| 132 | 30 | 1 (83%) | 0 (0%) |
| 5099 | 162 | 1 (83%) | 0 (0%) |
| A604 (IIIB) | 193 | 2 (16.7%) | 0 (0%) |
| p41-20 | 154 | 2 (16.7%) | 0 (0%) |
| A581 | 120 | 2 (16.7%) | 0 (0%) |
| A105 | 112 | 0 (0%) | 0 (0%) |
| 510 | 133 | 4 (33.3%) | 0 (0%) |
| 59 | 14 | 0 (0%) | 0 (0%) |
| 560 | 20 | 0 (0%) | 0 (0%) |
| 466 | 4 | 0 (0%) | 0 (0%) |
| RG-2 | 178 | 0 (0%) | 0 (0%) |
| 41-13 | 153 | 0 (0%) | 0 (0%) |
| A6938 | 135 | 0 (0%) | 0 (0%) |
| BS-1 | 114 | 0 (0%) | 0 (0%) |
| 35 | 5 | 0 (0%) | 0 (0%) |
| 120 | 21 | 0 (0%) | 0 (0%) |
| 117 | 19 | 2 (16.7%) | 0 (0%) |
| 97 | 13 | 2 (16.7%) | 0 (0%) |
| 99 | 106 | 0 (0%) | 0 (0%) |
| 41-11 | 157 | 0 (0%) | 0 (0%) |
| 41-21 | 152 | 0 (0%) | 0 (0%) |
| A405 | 130 | 1 (8.3%) | 0 (0%) |
| (2) 1/SP10IIIB | 194 | 8 (66.7%) | 1 (25%) |
| (2) T19V | 195 | 3 (25%) | 0 (0%) |
| (2) S19C | 196 | 0 (0%) | 0 (0%) |
| A487 | 132 | 1 (8.3%) | 0 (0%) |
| A733 | 174 | 1 (8.3%) | 0 (0%) |
| 41-12 | 151 | 12 (100%) | 4 (100%) |

[2] Indicates the synthetic peptides are described in the January 1991 Catalog referenced under Table 8. See pages 151, 154, 155.

Within this sample group, peptides C19Q SEQ ID NO:137] and 510 [SEQ ID NO:133] both bind to non-transmitter at least 30% without any binding of the transmitter samples (i.e. 0%). Additionally, AID-PND SEQ ID NO:134] and 1/SP10 IIIB [SEQ ID NO:194] also appear to selectively correlate with non-transmitters, as these two peptides bound greater than 50% of the nontransmitters and these percentages were at least two fold greater than binding exhibited by the transmitters.

Table 13 below illustrates sera binding to peptides, expressed in terms of the average number of peptides bound, for non-transmitter and transmitter group. The transmission versus non-transmission groups in these studies will be compared using the nonparametric Mann-Whitney test or student t-test.

TABLE 13

| | Avg. No. of Peptides Bound ± SD | | |
|---|---|---|---|
| | gp120 | gp41 | gp120 + gp 41 |
| Non-transmitters | 3.95 ± 1.91 | 2.56 ± 1.50 | 6.50 ± 2.35 |
| Transmitters | 2.64 ± 1.36* | 0.981 ± 1.14* | 3.55 ± 2.12* |

*Statistically decreased when compared to non-transmitters by t-test ($p < 0.05$).

These results indicate that the average number of peptides bound by sera from transmitting mothers is significantly lower than sera from non-transmitting mothers whether designated in terms of gp120 peptides only, gp41 peptides only, or gp 120+gp41 peptides combined, with the transmitter group being significantly lower.

EXAMPLE 7

Screening of Maternal Sera with Another Peptide Collection

This example provides additional sera screens using peptides corresponding to sequences of the MN strain. The sera samples (5 transmitters and 5 non-transmitters) were obtained from the NIH and differ from those screened in the previous studies. Peptide binding was analyzed by ELISA as described in Example 3. These results are provided in Table 14 below. This data reports on peptides of gp41 covering 67% of the gp41 transmembrane glycoprotein.

TABLE 14

| | | No. of Sera Samples Bound (% Bound) | |
|---|---|---|---|
| Peptide | Sequence ID No. | Non-Transmitter n = 5 | Transmitter n = 5 |
| MN-7 | 161 | 3 (60%) | 3 (60%) |
| MN-20 | 164 | 1 (20%) | 0 (0%) |
| MN-19 | 169 | 1 (20%) | 1 (20%) |
| MN-15 | 165 | 3 (60%) | 0 (0%) |
| MN-14 | 168 | 2 (40%) | 1 (20%) |
| MN-13 | 166 | 3 (60%) | 0 (0%) |
| MN-16 | 167 | 0 (0%) | 0 (0%) |
| 55 | 27 | 0 (0%) | 0 (0%) |
| 53 | 7 | 0 (0%) | 0 (0%) |
| MN-17 | 170 | 2 (40%) | 0 (0%) |
| MN-8 | 159 | 4 (80%) | 1 (20%) |
| MN-10 | 158 | 1 (20%) | 1 (20%) |
| MN-11 | 171 | 3 (60%) | 0 (0%) |
| MN-12 | 197 | 0 (0%) | 0 (0%) |
| MN-19 | 169 | 1 (20%) | 1 (20%) |

From this data, peptides MN-17, MN-8, MN-11 and MN-15 are shown to selectively correlate with non-transmission. This study further indicates that sera immunoglobulins from mothers who are non-transmitters have a broader reactivity to both gp120 and gp41 in terms of binding to peptides than do transmitter mothers.

Numerous modifications and variations of the present invention are included in the above-identified specification and are expected to be obvious to one of skill in the art. Such modifications and alterations to the methods of the present invention are believed to be encompassed in the scope of the claims appended hereto.

What is claimed is:

1. A method for determining whether or not a mother will transmit HIV-1 to a fetus in a given pregnancy comprising:
   (a) providing a biological sample from an HIV-infected woman;
   (b) incubating said sample with a collection of HIV peptides comprising at least one peptide selected from the group consisting of gp120-derived peptides:
   SEQ ID NO: 1: YDTEVHNVWATHACV,
   SEQ ID NO: 2: RKSIGIQRGPGR,
   SEQ ID NO: 3: KQFINMWQEVGKAMYAPP,
   SEQ ID NO: 4: CFRPGGGDMRDNWREL,
   SEQ ID NO: 10: TLPCASDAKAYDTEV,
   SEQ ID NO:137: CNNKTFNGTGFCTNVSTVQ,
   SEQ ID NO:133: VVQREKRAVGIG,
   SEQ ID NO:134: YNKRKRIHIQRGPGRAFYTTK-NII,
   SEQ ID NO:194: KQIINMWQEVGKAMYACTRP-NNNTRKSIRIQRGPG,
   and at least one peptide selected from the group consisting of gp41-derived peptides:
   SEQ ID NO: 5: QNNLLRAIEAQQHLLQLTVWGI,
   SEQ ID NO: 6: CQNQQEKNEQELLEL,
   SEQ ID NO: 7: ELDKWASLWNWFNITNWLWY,
   SEQ ID NO: 8: VTRIVELLGRRGWEALKYWW,
   SEQ ID NO: 30: FSYHRLRDLLLIVTR,
   SEQ ID NO: 31: NATAIAVAEGTDRVIEVVQGAY-RAI,
   SEQ ID NO: 121: LGIWGCSGKLIC,
   SEQ ID NO:170: YIKIFIMIVGGLVG,
   SEQ ID NO:159: DTSGRLVHGFLAIIW,
   SEQ ID NO:171: HIPTRIRQGLERALL, and
   SEQ ID NO:165: HMLQLTVWGIKQLQAR;
   (c) determining the number of peptides in said collection reacted with said sample;
   (d) comparing the number of reacting peptides to a standard, wherein said standard provides a pattern of peptide reaction with a sample from a patient of transmission status,
   wherein a non-transmissible HIV sample is indicated by reaction of said sample with at least about two fold more peptides than react with said standard.

2. A method for diagnosing HIV infection in an infant born to an HIV-infected mother comprising the steps of:
   (a) providing a sample from said HIV-infected woman or said infant;
   (b) incubating said sample with a collection of HIV peptides comprising at least one peptide selected from the group consisting of gp120-derived peptides:
   SEQ ID NO: 1: YDTEVHNVWATHACV,
   SEQ ID NO: 2: RKSIGIQRGPGR,
   SEQ ID NO: 3: KQFINMWQEVGKAMYAPP,
   SEQ ID NO: 4: CFRPGGGDMRDNWREL,
   SEQ ID NO: 10: TLPCASDAKAYDTEV,
   SEQ ID NO:137: CNNKTFNGTGFCTNVSTVQ,
   SEQ ID NO:133: VVQREKRAVGIG,
   SEQ ID NO:134: YNKRKRIHIQRGPGRAFYTTK-NII,
   SEQ ID NO:194: KQIINMWQEVGKAMYACTRPNNNTRK-SIRIQRGPG,
   and at least one peptide selected from the group consisting of gp41-derived peptides:
   SEQ ID NO: 5: ONNLLRAIEAQQHLLQLTVWGI,
   SEQ ID NO: 6: CQNQQEKNEQELLEL,
   SEQ ID NO: 7: ELDKASLWNWFNITNWLWY,
   SEQ ID NO: 8: VTRIVELLGRRGWEALKYWW,
   SEQ ID NO: 30: FSYHRLRDLLLIVTR,
   SEQ ID NO: 31: NATAIAVAEGTDRVIEVVQGAY-RAI,
   SEQ ID NO: 121: LGIWGCSGKLIC,
   SEQ ID NO:170: YIKIFIMIVGGLVG,
   SEQ ID NO:159: DTSGRLVHGFLAIIW,
   SEQ ID NO:171: HIPTRIRQGLERALL, and
   SEQ ID NO:165: HMLQLTVWGIKQLQAR;
   (c) determining the number of peptides reacting with said sample;
   (d) comparing the number of reacting peptides to a standard, wherein said standard provides a pattern of peptides reacting with a sample from a patient of transmission status,
   wherein non-transmission status is indicated by reaction with said sample of at least about two fold more peptides than react with said standard, and where the non-transmission status of the mother corresponds to the HIV diagnosis in the infant.

* * * * *

SEQUENCE LISTING ( 1 ) GENERAL INFORMATION:

( i i i ) NUMBER OF SEQUENCES: 197

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:1:

```
Tyr  Asp  Thr  Glu  Val  His  Asn  Val  Trp  Ala  Thr  His  Ala  Cys  Val
 1                  5                        10                       15
```

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:2:

```
Arg  Lys  Ser  Ile  Gly  Ile  Gln  Arg  Gly  Pro  Gly  Arg
 1                  5                        10
```

( 2 ) INFORMATION FOR SEQ ID NO:3:

( i ) SEQUENCE CHARACTERISTICS:
        ( A ) LENGTH: 18 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:3:

```
Lys  Gln  Phe  Ile  Asn  Met  Trp  Gln  Glu  Val  Gly  Lys  Ala  Met  Tyr  Ala
 1                  5                        10                       15
Pro  Pro
```

( 2 ) INFORMATION FOR SEQ ID NO:4:

( i ) SEQUENCE CHARACTERISTICS:
        ( A ) LENGTH: 16 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:4:

```
Cys  Phe  Arg  Pro  Gly  Gly  Gly  Asp  Met  Arg  Asp  Asn  Trp  Arg  Glu  Leu
 1                  5                        10                       15
```

( 2 ) INFORMATION FOR SEQ ID NO:5:

( i ) SEQUENCE CHARACTERISTICS:
        ( A ) LENGTH: 22 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:5:

```
        Gln  Asn  Asn  Leu  Leu  Arg  Ala  Ile  Glu  Ala  Gln  Gln  His  Leu  Leu  Gln
        1                 5                        10                       15

Leu  Thr  Val  Trp  Gly  Ile
                      20
```

( 2 ) INFORMATION FOR SEQ ID NO:6:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:6:

```
        Cys  Gln  Asn  Gln  Gln  Glu  Lys  Asn  Glu  Gln  Glu  Leu  Leu  Glu  Leu
        1                 5                        10                       15
```

( 2 ) INFORMATION FOR SEQ ID NO:7:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:7:

```
        Glu  Leu  Asp  Lys  Trp  Ala  Ser  Leu  Trp  Asn  Trp  Phe  Asn  Ile  Thr  Asn
        1                 5                        10                       15

Trp  Leu  Trp  Tyr
                      20
```

( 2 ) INFORMATION FOR SEQ ID NO:8:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:8:

```
        Val  Thr  Arg  Ile  Val  Glu  Leu  Leu  Gly  Arg  Arg  Gly  Trp  Glu  Ala  Leu
        1                 5                        10                       15

Lys  Tyr  Trp  Trp
                      20
```

( 2 ) INFORMATION FOR SEQ ID NO:9:

( i ) SEQUENCE CHARACTERISTICS:
        ( A ) LENGTH: 23 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:9:

```
        Ala  Thr  Glu  Lys  Leu  Trp  Val  Thr  Val  Tyr  Tyr  Gly  Val  Pro  Val  Trp
        1                 5                        10                       15

Leu  Glu  Ala  Thr  Thr  Thr  Leu
                      20
```

( 2 ) INFORMATION FOR SEQ ID NO:10:

( i ) SEQUENCE CHARACTERISTICS:

( A ) LENGTH: 15 amino acids
( B ) TYPE: amino acid
( D ) TOPOLOGY: unknown ( i i ) MOLECULE TYPE: peptide ( x i ) SEQUENCE DESCRIPTION: SEQ ID NO:10:

Thr Leu Pro Cys Ala Ser Asp Ala Lys Ala Tyr Asp Thr Glu Val
1               5                   10                  15

( 2 ) INFORMATION FOR SEQ ID NO:11:

( i ) SEQUENCE CHARACTERISTICS:
( A ) LENGTH: 15 amino acids
( B ) TYPE: amino acid
( D ) TOPOLOGY: unknown ( i i ) MOLECULE TYPE: peptide ( x i ) SEQUENCE DESCRIPTION: SEQ ID NO:11:

Thr His Ala Cys Val Pro Thr Asp Pro Asn Pro Gln Glu Val Val
1               5                   10                  15

( 2 ) INFORMATION FOR SEQ ID NO:12:

( i ) SEQUENCE CHARACTERISTICS:
( A ) LENGTH: 16 amino acids
( B ) TYPE: amino acid
( D ) TOPOLOGY: unknown ( i i ) MOLECULE TYPE: peptide ( x i ) SEQUENCE DESCRIPTION: SEQ ID NO:12:

Pro Gln Glu Val Val Leu Val Asn Val Thr Gly Glu Asn Phe Asn Met
1               5                   10                  15

( 2 ) INFORMATION FOR SEQ ID NO:13:

( i ) SEQUENCE CHARACTERISTICS:
( A ) LENGTH: 15 amino acids
( B ) TYPE: amino acid
( D ) TOPOLOGY: unknown ( i i ) MOLECULE TYPE: peptide ( x i ) SEQUENCE DESCRIPTION: SEQ ID NO:13:

Val Ser Leu Lys Cys Thr Asp Leu Lys Asn Asp Thr Asn Thr Asn
1               5                   10                  15

( 2 ) INFORMATION FOR SEQ ID NO:14:

( i ) SEQUENCE CHARACTERISTICS:
( A ) LENGTH: 21 amino acids
( B ) TYPE: amino acid
( D ) TOPOLOGY: unknown ( i i ) MOLECULE TYPE: peptide ( x i ) SEQUENCE DESCRIPTION: SEQ ID NO:14:

Ser Ser Gly Arg Met Ile Met Glu Lys Gly Glu Ile Lys Asn Cys Ser
1               5                   10                  15

Phe Asn Ile Ser Thr
                20

( 2 ) INFORMATION FOR SEQ ID NO:15:

( i ) SEQUENCE CHARACTERISTICS:
( A ) LENGTH: 15 amino acids
( B ) TYPE: amino acid (D) TOPOLOGY: unknown (ii) MOLECULE TYPE: peptide (xi) SEQUENCE DESCRIPTION: SEQ ID NO:15:

Cys Thr Arg Pro Asn Asn Asn Thr Arg Lys Ser Ile Arg Ile Gln
1               5                   10                  15

(2) INFORMATION FOR SEQ ID NO:16:

(i) SEQUENCE CHARACTERISTICS:
    (A) LENGTH: 15 amino acids
    (B) TYPE: amino acid
    (D) TOPOLOGY: unknown (ii) MOLECULE TYPE: peptide (xi) SEQUENCE DESCRIPTION: SEQ ID NO:16:

Thr Arg Lys Ser Ile Arg Ile Gln Arg Gly Pro Gly Arg Ala Phe
1               5                   10                  15

(2) INFORMATION FOR SEQ ID NO:17:

(i) SEQUENCE CHARACTERISTICS:
    (A) LENGTH: 15 amino acids
    (B) TYPE: amino acid
    (D) TOPOLOGY: unknown (ii) MOLECULE TYPE: peptide (xi) SEQUENCE DESCRIPTION: SEQ ID NO:17:

Arg Ile Gln Arg Gly Pro Gly Arg Ala Phe Val Thr Ile Gly Lys
1               5                   10                  15

(2) INFORMATION FOR SEQ ID NO:18:

(i) SEQUENCE CHARACTERISTICS:
    (A) LENGTH: 14 amino acids
    (B) TYPE: amino acid
    (D) TOPOLOGY: unknown (ii) MOLECULE TYPE: peptide (xi) SEQUENCE DESCRIPTION: SEQ ID NO:18:

Cys Thr Lys Ala Lys Arg Arg Val Val Gln Arg Glu Lys Ala
1               5                   10

(2) INFORMATION FOR SEQ ID NO:19:

(i) SEQUENCE CHARACTERISTICS:
    (A) LENGTH: 14 amino acids
    (B) TYPE: amino acid
    (D) TOPOLOGY: unknown (ii) MOLECULE TYPE: peptide (xi) SEQUENCE DESCRIPTION: SEQ ID NO:19:

Ile Gly Ala Leu Phe Leu Gly Phe Gly Ala Ala Gly Ser Thr
1               5                   10

(2) INFORMATION FOR SEQ ID NO:20:

(i) SEQUENCE CHARACTERISTICS:
    (A) LENGTH: 30 amino acids
    (B) TYPE: amino acid
    (D) TOPOLOGY: unknown (ii) MOLECULE TYPE: peptide (xi) SEQUENCE DESCRIPTION: SEQ ID NO:20:

```
    Cys  Ile  Val  Gln  Gln  Asn  Asn  Leu  Leu  Arg  Ala  Ile  Glu  Ala  Gln
    1                 5                      10                      15

Gln  His  Leu  Leu  Gln  Leu  Thr  Val  Trp  Gly  Ile  Lys  Gln  Leu
                   20                      25                      30
```

( 2 ) INFORMATION FOR SEQ ID NO:21:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:21:

```
    Trp  Gly  Ile  Lys  Gln  Leu  Gln  Ala  Arg  Ile  Leu  Ala  Val  Glu  Arg
    1                 5                      10                      15
```

( 2 ) INFORMATION FOR SEQ ID NO:22:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:22:

```
    Leu  Ala  Val  Glu  Arg  Tyr  Leu  Lys  Asp  Gln  Gln  Leu  Leu  Gly  Ile
    1                 5                      10                      15
```

( 2 ) INFORMATION FOR SEQ ID NO:23:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:23:

```
    Lys  Leu  Ile  Cys  Thr  Thr  Gln  Val  Pro  Trp  Asn  Ala  Ser  Trp  Ser
    1                 5                      10                      15
```

( 2 ) INFORMATION FOR SEQ ID NO:24:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:24:

```
    Ala  Ser  Trp  Ser  Asn  Lys  Ser  Leu  Glu  Gln  Ile  Trp  Asn  Asn  Met
    1                 5                      10                      15
```

( 2 ) INFORMATION FOR SEQ ID NO:25:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:25:

```
    Asp  Arg  Glu  Ile  Asn  Asn  Tyr  Thr  Ser  Leu  Ile  His  Ser  Leu  Ile
```

( 2 ) INFORMATION FOR SEQ ID NO:26:

( i ) SEQUENCE CHARACTERISTICS:
        ( A ) LENGTH: 16 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:26:

```
Asn Tyr Thr Ser Leu Ile His Ser Leu Ile Glu Glu Ser Gln Asn Gln
1               5                   10                  15
```

( 2 ) INFORMATION FOR SEQ ID NO:27:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:27:

```
Leu Arg Ile Val Phe Ala Val Leu Ser Val Val Asn Arg Val Arg Gln
1               5                   10                  15
Gly Tyr Ser Pro
                20
```

( 2 ) INFORMATION FOR SEQ ID NO:28:

( i ) SEQUENCE CHARACTERISTICS:
        ( A ) LENGTH: 14 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:28:

```
Gly Tyr Ser Pro Leu Ser Phe Gln Thr His Pro Ile Pro Arg
1               5                   10
```

( 2 ) INFORMATION FOR SEQ ID NO:29:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:29:

```
Glu Gly Gly Glu Arg Asp Arg Asp Arg Ser Ile Arg Leu Val Asn
1               5                   10                  15
```

( 2 ) INFORMATION FOR SEQ ID NO:30:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:30:

```
Phe Ser Tyr His Arg Leu Arg Asp Leu Leu Leu Ile Val Thr Arg
1               5                   10                  15
```

( 2 ) INFORMATION FOR SEQ ID NO:31:

( i ) SEQUENCE CHARACTERISTICS:
        ( A ) LENGTH: 25 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:31:

```
Asn Ala Thr Ala Ile Ala Val Ala Glu Gly Thr Asp Arg Val Ile Glu
 1               5                  10                  15
Val Val Gln Gly Ala Tyr Arg Ala Ile
             20                  25
```

( 2 ) INFORMATION FOR SEQ ID NO:32:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:32:

```
Met Arg Val Lys Gly Ile Arg Arg Asn Tyr Gln His Trp Trp Gly Trp
 1               5                  10                  15
Gly Thr Met Leu
             20
```

( 2 ) INFORMATION FOR SEQ ID NO:33:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:33:

```
Glu Lys Leu Trp Val Thr Val Tyr Tyr Gly Val Pro Val Trp Lys Glu
 1               5                  10                  15
Ala Thr Thr Thr
             20
```

( 2 ) INFORMATION FOR SEQ ID NO:34:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:34:

```
Val Pro Val Trp Lys Glu Ala Thr Thr Thr Leu Phe Cys Ala Ser Asp
 1               5                  10                  15
Ala Lys Ala Tyr
             20
```

( 2 ) INFORMATION FOR SEQ ID NO:35:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:35:

```
Asp Thr Glu Val His Asn Val Trp Ala Thr Gln Ala Cys Val Pro Thr
1               5                   10                  15
Asp Pro Asn Pro
            20
```

( 2 ) INFORMATION FOR SEQ ID NO:36:

( i ) SEQUENCE CHARACTERISTICS:
     ( A ) LENGTH: 13 amino acids
     ( B ) TYPE: amino acid
     ( D ) TOPOLOGY: unknown ( i i ) MOLECULE TYPE: peptide ( x i ) SEQUENCE DESCRIPTION: SEQ ID NO:36:

```
Glu Leu Val Asn Val Thr Glu Asn Phe Asn Met Trp Lys
1               5                   10
```

( 2 ) INFORMATION FOR SEQ ID NO:37:

( i ) SEQUENCE CHARACTERISTICS:
     ( A ) LENGTH: 20 amino acids
     ( B ) TYPE: amino acid
     ( D ) TOPOLOGY: unknown ( i i ) MOLECULE TYPE: peptide ( x i ) SEQUENCE DESCRIPTION: SEQ ID NO:37:

```
Asn Phe Asn Met Trp Lys Asn Asn Met Val Glu Gln Met His Glu Asp
1               5                   10                  15
Ile Ile Ser Leu
            20
```

( 2 ) INFORMATION FOR SEQ ID NO:38:

( i ) SEQUENCE CHARACTERISTICS:
     ( A ) LENGTH: 20 amino acids
     ( B ) TYPE: amino acid
     ( D ) TOPOLOGY: unknown ( i i ) MOLECULE TYPE: peptide ( x i ) SEQUENCE DESCRIPTION: SEQ ID NO:38:

```
Glu Gln Met His Glu Asp Ile Ile Ser Leu Trp Asp Gln Ser Leu Lys
1               5                   10                  15
Pro Cys Val Lys
            20
```

( 2 ) INFORMATION FOR SEQ ID NO:39:

( i ) SEQUENCE CHARACTERISTICS:
     ( A ) LENGTH: 20 amino acids
     ( B ) TYPE: amino acid
     ( D ) TOPOLOGY: unknown ( i i ) MOLECULE TYPE: peptide ( x i ) SEQUENCE DESCRIPTION: SEQ ID NO:39:

```
Trp Asp Gln Ser Leu Lys Pro Cys Val Lys Leu Thr Pro Leu Cys Val
1               5                   10                  15
Thr Leu Asn Cys
            20
```

( 2 ) INFORMATION FOR SEQ ID NO:40:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:40:

```
Leu Thr Pro Leu Cys Val Thr Leu Asn Cys Thr Asp Leu Arg Asn Thr
1               5                   10                  15
Thr Asn Thr Asn
            20
```

( 2 ) INFORMATION FOR SEQ ID NO:41:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:41:

```
Thr Asp Leu Arg Asn Thr Thr Asn Thr Asn Asn Ser Thr Ala Asn Asn
1               5                   10                  15
Asn Ser Asn Ser
            20
```

( 2 ) INFORMATION FOR SEQ ID NO:42:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:42:

```
Asn Ser Thr Ala Asn Asn Asn Ser Asn Ser Glu Gly Thr Ile Lys Gly
1               5                   10                  15
Gly Glu Met Lys
            20
```

( 2 ) INFORMATION FOR SEQ ID NO:43:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:43:

```
Glu Gly Thr Ile Lys Gly Gly Glu Met Lys Asn Cys Ser Phe Asn Ile
1               5                   10                  15
Thr Thr Ser Ile
            20
```

( 2 ) INFORMATION FOR SEQ ID NO:44:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:44:

Asn Cys Ser Phe Asn Ile Thr Thr Ser Ile Arg Asp Lys Met Gln Lys
1               5                   10                  15

Glu Tyr Ala Leu
            20

( 2 ) INFORMATION FOR SEQ ID NO:45:

( i ) SEQUENCE CHARACTERISTICS:
      ( A ) LENGTH: 20 amino acids
      ( B ) TYPE: amino acid
      ( D ) TOPOLOGY: unknown ( i i ) MOLECULE TYPE: peptide ( x i ) SEQUENCE DESCRIPTION: SEQ ID NO:45:

Arg Asp Lys Met Gln Lys Glu Tyr Ala Leu Leu Tyr Lys Leu Asp Ile
1               5                   10                  15

Val Ser Ile Asp
            20

( 2 ) INFORMATION FOR SEQ ID NO:46:

( i ) SEQUENCE CHARACTERISTICS:
      ( A ) LENGTH: 20 amino acids
      ( B ) TYPE: amino acid
      ( D ) TOPOLOGY: unknown ( i i ) MOLECULE TYPE: peptide ( x i ) SEQUENCE DESCRIPTION: SEQ ID NO:46:

Leu Tyr Lys Leu Asp Ile Val Ser Ile Asp Asn Asp Ser Thr Ser Tyr
1               5                   10                  15

Arg Leu Ile Ser
            20

( 2 ) INFORMATION FOR SEQ ID NO:47:

( i ) SEQUENCE CHARACTERISTICS:
      ( A ) LENGTH: 20 amino acids
      ( B ) TYPE: amino acid
      ( D ) TOPOLOGY: unknown ( i i ) MOLECULE TYPE: peptide ( x i ) SEQUENCE DESCRIPTION: SEQ ID NO:47:

Cys Asn Thr Ser Val Ile Thr Gln Ala Cys Pro Lys Ile Ser Phe Glu
1               5                   10                  15

Pro Ile Pro Ile
            20

( 2 ) INFORMATION FOR SEQ ID NO:48:

( i ) SEQUENCE CHARACTERISTICS:
      ( A ) LENGTH: 20 amino acids
      ( B ) TYPE: amino acid
      ( D ) TOPOLOGY: unknown ( i i ) MOLECULE TYPE: peptide ( x i ) SEQUENCE DESCRIPTION: SEQ ID NO:48:

Pro Lys Ile Ser Phe Glu Pro Ile Pro Ile His Tyr Cys Ala Pro Ala
1               5                   10                  15

Gly Phe Ala Ile
            20

( 2 ) INFORMATION FOR SEQ ID NO:49:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:49:

```
His Tyr Cys Ala Pro Ala Gly Phe Ala Ile Leu Lys Cys Asn Asp Lys
1               5                   10                  15

Lys Phe Ser Gly
            20
```

( 2 ) INFORMATION FOR SEQ ID NO:50:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:50:

```
Leu Lys Cys Asn Asp Lys Lys Phe Ser Gly Lys Gly Ser Cys Lys Asn
1               5                   10                  15

Val Ser Thr Val
            20
```

( 2 ) INFORMATION FOR SEQ ID NO:51:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:51:

```
Lys Gly Ser Cys Lys Asn Val Ser Thr Val Gln Cys Thr His Gly Ile
1               5                   10                  15

Arg Pro Val Val
            20
```

( 2 ) INFORMATION FOR SEQ ID NO:52:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:52:

```
Gln Cys Thr His Gly Ile Arg Pro Val Val Ser Thr Gln Leu Leu Leu
1               5                   10                  15

Asn Gly Ser Leu
            20
```

( 2 ) INFORMATION FOR SEQ ID NO:53:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:53:

Ser Thr Gln Leu Leu Leu Asn Gly Ser Leu Ala Glu Glu Glu Val Val
1               5                   10                  15

Ile Arg Ser Glu
            20

( 2 ) INFORMATION FOR SEQ ID NO:54:

( i ) SEQUENCE CHARACTERISTICS:
    ( A ) LENGTH: 20 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:54:

Ala Glu Glu Glu Val Val Ile Arg Ser Glu Asn Phe Thr Asp Asn Ala
1               5                   10                  15

Lys Thr Ile Ile
            20

( 2 ) INFORMATION FOR SEQ ID NO:55:

( i ) SEQUENCE CHARACTERISTICS:
    ( A ) LENGTH: 20 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:55:

Asn Phe Thr Asp Asn Ala Lys Thr Ile Ile Val His Leu Asn Glu Ser
1               5                   10                  15

Val Gln Ile Asn
            20

( 2 ) INFORMATION FOR SEQ ID NO:56:

( i ) SEQUENCE CHARACTERISTICS:
    ( A ) LENGTH: 20 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:56:

Val His Leu Asn Glu Ser Val Gln Ile Asn Cys Thr Arg Pro Asn Tyr
1               5                   10                  15

Asn Lys Arg Lys
            20

( 2 ) INFORMATION FOR SEQ ID NO:57:

( i ) SEQUENCE CHARACTERISTICS:
    ( A ) LENGTH: 20 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:57:

Cys Thr Arg Pro Asn Tyr Asn Lys Arg Lys Arg Ile His Ile Gly Pro
1               5                   10                  15

```
          Gly  Arg  Ala  Phe
                         20
```

( 2 ) INFORMATION FOR SEQ ID NO:58:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:58:

```
Arg  Ile  His  Ile  Gly  Pro  Gly  Arg  Ala  Phe  Tyr  Thr  Thr  Lys  Asn  Ile
1                        5                        10                       15

Ile  Gly  Thr  Ile
               20
```

( 2 ) INFORMATION FOR SEQ ID NO:59:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:59:

```
Tyr  Thr  Thr  Lys  Asn  Ile  Ile  Gly  Thr  Ile  Arg  Gln  Ala  His  Cys  Asn
1                        5                        10                       15

Ile  Ser  Arg  Ala
               20
```

( 2 ) INFORMATION FOR SEQ ID NO:60:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:60:

```
Arg  Gln  Ala  His  Cys  Asn  Ile  Ser  Arg  Ala  Lys  Trp  Asn  Asp  Thr  Leu
1                        5                        10                       15

Arg  Gln  Ile  Val
               20
```

( 2 ) INFORMATION FOR SEQ ID NO:61:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:61:

```
Lys  Trp  Asn  Asp  Thr  Leu  Arg  Gln  Ile  Val  Ser  Lys  Leu  Lys  Glu  Gln
1                        5                        10                       15

Phe  Lys  Asn  Lys
               20
```

( 2 ) INFORMATION FOR SEQ ID NO:62:

( i ) SEQUENCE CHARACTERISTICS:
        ( A ) LENGTH: 20 amino acids ( B ) TYPE: amino acid
( D ) TOPOLOGY: unknown ( i i ) MOLECULE TYPE: peptide ( x i ) SEQUENCE DESCRIPTION: SEQ ID NO:62:

```
Ser Lys Leu Lys Glu Gln Phe Lys Asn Lys Thr Ile Val Phe Asn Gln
1               5                   10                  15
Ser Ser Gly Gly
            20
```

( 2 ) INFORMATION FOR SEQ ID NO:63:

( i ) SEQUENCE CHARACTERISTICS:
( A ) LENGTH: 20 amino acids
( B ) TYPE: amino acid
( D ) TOPOLOGY: unknown ( i i ) MOLECULE TYPE: peptide ( x i ) SEQUENCE DESCRIPTION: SEQ ID NO:63:

```
Thr Ile Val Phe Asn Gln Ser Ser Gly Gly Asp Pro Glu Ile Val Met
1               5                   10                  15
His Ser Phe Asn
            20
```

( 2 ) INFORMATION FOR SEQ ID NO:64:

( i ) SEQUENCE CHARACTERISTICS:
( A ) LENGTH: 20 amino acids
( B ) TYPE: amino acid
( D ) TOPOLOGY: unknown ( i i ) MOLECULE TYPE: peptide ( x i ) SEQUENCE DESCRIPTION: SEQ ID NO:64:

```
Cys Gly Gly Glu Phe Phe Tyr Cys Asn Thr Ser Pro Leu Phe Asn Ser
1               5                   10                  15
Thr Trp Asn Gly
            20
```

( 2 ) INFORMATION FOR SEQ ID NO:65:

( i ) SEQUENCE CHARACTERISTICS:
( A ) LENGTH: 20 amino acids
( B ) TYPE: amino acid
( D ) TOPOLOGY: unknown ( i i ) MOLECULE TYPE: peptide ( x i ) SEQUENCE DESCRIPTION: SEQ ID NO:65:

```
Ser Pro Leu Phe Asn Ser Thr Trp Asn Gly Asn Asn Thr Trp Asn Asn
1               5                   10                  15
Thr Thr Gly Ser
            20
```

( 2 ) INFORMATION FOR SEQ ID NO:66:

( i ) SEQUENCE CHARACTERISTICS:
( A ) LENGTH: 14 amino acids
( B ) TYPE: amino acid
( D ) TOPOLOGY: unknown ( i i ) MOLECULE TYPE: peptide ( x i ) SEQUENCE DESCRIPTION: SEQ ID NO:66:

```
Asn Thr Thr Gly Ser Asn Asn Asn Ile Thr Leu Gln Cys Lys
```

( 2 ) INFORMATION FOR SEQ ID NO:67:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:67:

```
Lys Gln Ile Ile Asn Met Trp Gln Glu Val Gly Lys Ala Met Tyr Ala
 1               5                  10                  15
Pro Pro Ile Glu
            20
```

( 2 ) INFORMATION FOR SEQ ID NO:68:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:68:

```
Gly Lys Ala Met Tyr Ala Pro Pro Ile Glu Gly Gln Ile Arg Cys Ser
 1               5                  10                  15
Ser Asn Ile Thr
            20
```

( 2 ) INFORMATION FOR SEQ ID NO:69:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:69:

```
Asp Thr Asp Thr Asn Asp Thr Glu Ile Phe Arg Pro Gly Gly Gly Asp
 1               5                  10                  15
Met Arg Asp Asn
            20
```

( 2 ) INFORMATION FOR SEQ ID NO:70:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:70:

```
Arg Pro Gly Gly Gly Asp Met Arg Asp Asn Trp Arg Ser Glu Leu Tyr
 1               5                  10                  15
Lys Tyr Lys Val
            20
```

( 2 ) INFORMATION FOR SEQ ID NO:71:

( i ) SEQUENCE CHARACTERISTICS:
        ( A ) LENGTH: 20 amino acids
        ( B ) TYPE: amino acid -continued ( D ) TOPOLOGY: unknown ( i i ) MOLECULE TYPE: peptide ( x i ) SEQUENCE DESCRIPTION: SEQ ID NO:71:

```
Trp Arg Ser Glu Leu Tyr Lys Tyr Lys Val Val Thr Ile Glu Pro Leu
1               5                   10                  15
Gly Val Ala Pro
            20
```

( 2 ) INFORMATION FOR SEQ ID NO:72:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:72:

```
Val Thr Ile Glu Pro Leu Gly Val Ala Pro Thr Lys Ala Lys Arg Arg
1               5                   10                  15
Val Val Gln Arg
            20
```

( 2 ) INFORMATION FOR SEQ ID NO:73:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:73:

```
Thr Lys Ala Lys Arg Arg Val Val Gln Arg Glu Lys Arg Ala Ala Ile
1               5                   10                  15
Gly Ala Leu Phe
            20
```

( 2 ) INFORMATION FOR SEQ ID NO:74:

( i ) SEQUENCE CHARACTERISTICS:
        ( A ) LENGTH: 12 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:74:

```
Leu Phe Leu Gly Phe Leu Gly Ala Ala Gly Ser Thr
1               5                   10
```

( 2 ) INFORMATION FOR SEQ ID NO:75:

( i ) SEQUENCE CHARACTERISTICS:
        ( A ) LENGTH: 11 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:75:

```
Gly Ala Ala Gly Ser Thr Met Gly Ala Ala Ser
1               5                   10
```

( 2 ) INFORMATION FOR SEQ ID NO:76:

( i ) SEQUENCE CHARACTERISTICS:
  ( A ) LENGTH: 20 amino acids
  ( B ) TYPE: amino acid
  ( D ) TOPOLOGY: unknown ( i i ) MOLECULE TYPE: peptide ( x i ) SEQUENCE DESCRIPTION: SEQ ID NO:76:

```
Gln Ala Arg Leu Leu Leu Ser Gly Ile Val Gln Gln Gln Asn Asn Leu
1               5                   10                  15
Leu Arg Ala Ile
            20
```

( 2 ) INFORMATION FOR SEQ ID NO:77:

( i ) SEQUENCE CHARACTERISTICS:
    ( A ) LENGTH: 20 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:77:

```
Gln Gln Gln Asn Asn Leu Leu Arg Ala Ile Glu Ala Gln Gln His Met
1               5                   10                  15
Leu Gln Leu Thr
            20
```

( 2 ) INFORMATION FOR SEQ ID NO:78:

( i ) SEQUENCE CHARACTERISTICS:
    ( A ) LENGTH: 20 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:78:

```
Glu Ala Gln Gln His Met Leu Gln Leu Thr Val Trp Gly Ile Lys Gln
1               5                   10                  15
Leu Gln Ala Arg
            20
```

( 2 ) INFORMATION FOR SEQ ID NO:79:

( i ) SEQUENCE CHARACTERISTICS:
    ( A ) LENGTH: 20 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:79:

```
Val Trp Gly Ile Lys Gln Leu Gln Ala Arg Val Leu Ala Val Glu Arg
1               5                   10                  15
Tyr Leu Lys Asp
            20
```

( 2 ) INFORMATION FOR SEQ ID NO:80:

( i ) SEQUENCE CHARACTERISTICS:
    ( A ) LENGTH: 12 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:80:

Glu Arg Tyr Leu Lys Asp Gln Gln Leu Leu Gly Phe
1               5                   10

( 2 ) INFORMATION FOR SEQ ID NO:81:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:81:

Gly Lys Leu Ile Cys Thr Thr Thr Val Pro Trp Asn Ala Ser Trp Ser
1               5                   10                  15

Asn Lys Ser Leu
            20

( 2 ) INFORMATION FOR SEQ ID NO:82:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:82:

Asp Asp Ile Trp Asn Asn Met Thr Trp Met Gln Trp Glu Arg Glu Ile
1               5                   10                  15

Asp Asn Tyr Thr
            20

( 2 ) INFORMATION FOR SEQ ID NO:83:

( i ) SEQUENCE CHARACTERISTICS:
        ( A ) LENGTH: 18 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:83:

Glu Arg Glu Ile Asp Asn Tyr Thr Ser Leu Ile Tyr Ser Leu Leu Glu
1               5                   10                  15

Lys Ser ( 2 ) INFORMATION FOR SEQ ID NO:84:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:84:

Ser Leu Ile Tyr Ser Leu Leu Glu Lys Ser Gln Thr Gln Gln Glu Lys
1               5                   10                  15

Asn Glu Gln Glu
            20

( 2 ) INFORMATION FOR SEQ ID NO:85:

( i ) SEQUENCE CHARACTERISTICS:

(A) LENGTH: 20 amino acids
(B) TYPE: amino acid
(D) TOPOLOGY: unknown (ii) MOLECULE TYPE: peptide (xi) SEQUENCE DESCRIPTION: SEQ ID NO:85:

Gln Thr Gln Gln Glu Lys Asn Glu Gln Glu Leu Leu Glu Leu Asp Lys
1               5                   10                  15
Trp Ala Ser Leu
            20

(2) INFORMATION FOR SEQ ID NO:86:

(i) SEQUENCE CHARACTERISTICS:
    (A) LENGTH: 20 amino acids
    (B) TYPE: amino acid
    (D) TOPOLOGY: unknown (ii) MOLECULE TYPE: peptide (xi) SEQUENCE DESCRIPTION: SEQ ID NO:86:

Leu Leu Glu Leu Asp Lys Trp Ala Ser Leu Trp Asn Trp Phe Asp Ile
1               5                   10                  15
Thr Asn Trp Leu
            20

(2) INFORMATION FOR SEQ ID NO:87:

(i) SEQUENCE CHARACTERISTICS:
    (A) LENGTH: 20 amino acids
    (B) TYPE: amino acid
    (D) TOPOLOGY: unknown (ii) MOLECULE TYPE: peptide (xi) SEQUENCE DESCRIPTION: SEQ ID NO:87:

Ala Val Leu Ser Ile Val Asn Arg Val Arg Gln Gly Tyr Ser Pro Leu
1               5                   10                  15
Ser Leu Gln Thr
            20

(2) INFORMATION FOR SEQ ID NO:88:

(i) SEQUENCE CHARACTERISTICS:
    (A) LENGTH: 20 amino acids
    (B) TYPE: amino acid
    (D) TOPOLOGY: unknown (ii) MOLECULE TYPE: peptide (xi) SEQUENCE DESCRIPTION: SEQ ID NO:88:

Gln Gly Tyr Ser Pro Leu Ser Leu Gln Thr Arg Pro Pro Val Pro Arg
1               5                   10                  15
Gly Pro Asp Arg
            20

(2) INFORMATION FOR SEQ ID NO:89:

(i) SEQUENCE CHARACTERISTICS:
    (A) LENGTH: 20 amino acids
    (B) TYPE: amino acid
    (D) TOPOLOGY: unknown (ii) MOLECULE TYPE: peptide (xi) SEQUENCE DESCRIPTION: SEQ ID NO:89:

-continued

```
Arg  Pro  Pro  Val  Pro  Arg  Gly  Pro  Asp  Arg  Pro  Glu  Gly  Ile  Glu  Glu
1                  5                    10                      15

Glu  Gly  Gly  Glu
              20
```

( 2 ) INFORMATION FOR SEQ ID NO:90:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:90:

```
Pro  Glu  Gly  Ile  Glu  Glu  Glu  Gly  Gly  Glu  Arg  Asp  Arg  Asp  Thr  Arg
1                  5                    10                      15

Gly  Arg  Leu  Val
              20
```

( 2 ) INFORMATION FOR SEQ ID NO:91:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:91:

```
Arg  Asp  Arg  Asp  Thr  Arg  Gly  Arg  Leu  Val  His  Gly  Phe  Leu  Ala  Ile
1                  5                    10                      15

Ile  Trp  Val  Asp
              20
```

( 2 ) INFORMATION FOR SEQ ID NO:92:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:92:

```
Leu  Arg  Ser  Leu  Phe  Leu  Phe  Gly  Tyr  His  His  Arg  Asp  Leu  Leu  Leu
1                  5                    10                      15

Ile  Ala  Ala  Arg
              20
```

( 2 ) INFORMATION FOR SEQ ID NO:93:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:93:

```
His  Arg  Asp  Leu  Leu  Leu  Ile  Ala  Ala  Arg  Ile  Val  Glu  Leu  Leu  Gly
1                  5                    10                      15

Arg  Arg  Gly  Trp
              20
```

( 2 ) INFORMATION FOR SEQ ID NO:94:

( i ) SEQUENCE CHARACTERISTICS:
  ( A ) LENGTH: 20 amino acids
  ( B ) TYPE: amino acid
  ( D ) TOPOLOGY: unknown ( i i ) MOLECULE TYPE: peptide ( x i ) SEQUENCE DESCRIPTION: SEQ ID NO:94:

Ile Val Glu Leu Leu Gly Arg Arg Gly Trp Glu Val Leu Lys Tyr Trp
1               5                   10                  15

Trp Asn Leu Leu
            20

( 2 ) INFORMATION FOR SEQ ID NO:95:

( i ) SEQUENCE CHARACTERISTICS:
    ( A ) LENGTH: 20 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:95:

Glu Val Leu Lys Tyr Trp Trp Asn Leu Leu Gln Tyr Trp Ser Gln Glu
1               5                   10                  15

Leu Lys Ser Ser
            20

( 2 ) INFORMATION FOR SEQ ID NO:96:

( i ) SEQUENCE CHARACTERISTICS:
    ( A ) LENGTH: 19 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:96:

Ala Val Glu Gly Thr Asp Arg Val Ile Glu Val Leu Gln Arg Ala Gly
1               5                   10                  15

Arg Ala Ile ( 2 ) INFORMATION FOR SEQ ID NO:97:

( i ) SEQUENCE CHARACTERISTICS:
    ( A ) LENGTH: 20 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:97:

Glu Val Leu Gln Arg Ala Gly Arg Ala Ile Leu His Ile Pro Thr Arg
1               5                   10                  15

Ile Arg Gln Gly
            20

( 2 ) INFORMATION FOR SEQ ID NO:98:

( i ) SEQUENCE CHARACTERISTICS:
    ( A ) LENGTH: 16 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:98:

Leu His Ile Pro Thr Arg Ile Arg Gln Gly Leu Glu Arg Ala Leu Leu
1               5                   10                  15

( 2 ) INFORMATION FOR SEQ ID NO:99:

( i ) SEQUENCE CHARACTERISTICS:
      ( A ) LENGTH: 15 amino acids
      ( B ) TYPE: amino acid
      ( D ) TOPOLOGY: unknown ( i i ) MOLECULE TYPE: peptide ( x i ) SEQUENCE DESCRIPTION: SEQ ID NO:99:

Phe Asn Met Trp Lys Asn Asp Met Val Glu Gln Met His Glu Asp
1               5                   10                  15

( 2 ) INFORMATION FOR SEQ ID NO:100:

( i ) SEQUENCE CHARACTERISTICS:
      ( A ) LENGTH: 15 amino acids
      ( B ) TYPE: amino acid
      ( D ) TOPOLOGY: unknown ( i i ) MOLECULE TYPE: peptide ( x i ) SEQUENCE DESCRIPTION: SEQ ID NO:100:

Asn Asp Met Val Glu Gln Met His Glu Asp Ile Ile Ser Leu Trp
1               5                   10                  15

( 2 ) INFORMATION FOR SEQ ID NO:101:

( i ) SEQUENCE CHARACTERISTICS:
      ( A ) LENGTH: 15 amino acids
      ( B ) TYPE: amino acid
      ( D ) TOPOLOGY: unknown ( i i ) MOLECULE TYPE: peptide ( x i ) SEQUENCE DESCRIPTION: SEQ ID NO:101:

Glu Gln Met His Glu Asp Ile Ile Ser Leu Trp Asp Gln Ser Leu
1               5                   10                  15

( 2 ) INFORMATION FOR SEQ ID NO:102:

( i ) SEQUENCE CHARACTERISTICS:
      ( A ) LENGTH: 13 amino acids
      ( B ) TYPE: amino acid
      ( D ) TOPOLOGY: unknown ( i i ) MOLECULE TYPE: peptide ( x i ) SEQUENCE DESCRIPTION: SEQ ID NO:102:

His Glu Asp Ile Ile Ser Leu Trp Asp Gln Ser Leu Lys
1               5                   10

( 2 ) INFORMATION FOR SEQ ID NO:103:

( i ) SEQUENCE CHARACTERISTICS:
      ( A ) LENGTH: 15 amino acids
      ( B ) TYPE: amino acid
      ( D ) TOPOLOGY: unknown ( i i ) MOLECULE TYPE: peptide ( x i ) SEQUENCE DESCRIPTION: SEQ ID NO:103:

Asp Ile Ile Ser Leu Trp Asp Gln Ser Leu Lys Pro Cys Val Lys
1               5                   10                  15

( 2 ) INFORMATION FOR SEQ ID NO:104:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:104:

```
Asn  Ser  Ser  Ser  Gly  Arg  Met  Ile  Met  Glu  Lys  Gly  Glu  Ile  Lys
1                   5                        10                       15
```

( 2 ) INFORMATION FOR SEQ ID NO:105:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:105:

```
Cys  Ser  Phe  Asn  Ile  Ser  Thr  Ser  Ile  Arg  Gly  Lys  Val  Gln  Lys
1                   5                        10                       15
```

( 2 ) INFORMATION FOR SEQ ID NO:106:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:106:

```
Ile  Ile  Pro  Ile  Asp  Asn  Asp  Thr  Thr  Ser  Tyr  Ser  Leu  Thr  Ser
1                   5                        10                       15
```

( 2 ) INFORMATION FOR SEQ ID NO:107:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:107:

```
Ile  Thr  Gln  Ala  Cys  Pro  Lys  Val  Ser  Phe  Glu  Pro  Ile  Pro  Ile
1                   5                        10                       15
```

( 2 ) INFORMATION FOR SEQ ID NO:108:

( i ) SEQUENCE CHARACTERISTICS:
        ( A ) LENGTH: 18 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:108:

```
Phe  Glu  Pro  Ile  Pro  Ile  His  Tyr  Cys  Ala  Pro  Ala  Gly  Phe  Ala  Ile
1                   5                        10                       15
Leu  Lys
```

( 2 ) INFORMATION FOR SEQ ID NO:109:

( i ) SEQUENCE CHARACTERISTICS:

(A) LENGTH: 15 amino acids
(B) TYPE: amino acid
(D) TOPOLOGY: unknown (ii) MOLECULE TYPE: peptide (xi) SEQUENCE DESCRIPTION: SEQ ID NO:109:

```
Ala Gly Phe Ala Ile Leu Lys Cys Asn Asn Lys Thr Phe Asn Gly
1               5                   10                  15
```

(2) INFORMATION FOR SEQ ID NO:110:

(i) SEQUENCE CHARACTERISTICS:
(A) LENGTH: 22 amino acids
(B) TYPE: amino acid
(D) TOPOLOGY: unknown (ii) MOLECULE TYPE: peptide (xi) SEQUENCE DESCRIPTION: SEQ ID NO:110:

```
Gln Cys Thr His Gly Ile Arg Pro Val Val Ser Thr Gln Leu Leu Leu
1               5                   10                  15
Asn Gly Ser Leu Ala Glu
                20
```

(2) INFORMATION FOR SEQ ID NO:111:

(i) SEQUENCE CHARACTERISTICS:
(A) LENGTH: 16 amino acids
(B) TYPE: amino acid
(D) TOPOLOGY: unknown (ii) MOLECULE TYPE: peptide (xi) SEQUENCE DESCRIPTION: SEQ ID NO:111:

```
Glu Glu Glu Val Val Ile Arg Ser Val Asn Phe Thr Asp Asn Ala Lys
1               5                   10                  15
```

(2) INFORMATION FOR SEQ ID NO:112:

(i) SEQUENCE CHARACTERISTICS:
(A) LENGTH: 15 amino acids
(B) TYPE: amino acid
(D) TOPOLOGY: unknown (ii) MOLECULE TYPE: peptide (xi) SEQUENCE DESCRIPTION: SEQ ID NO:112:

```
Val Gln Leu Asn Thr Ser Val Glu Ile Asn Cys Thr Arg Pro Asn
1               5                   10                  15
```

(2) INFORMATION FOR SEQ ID NO:113:

(i) SEQUENCE CHARACTERISTICS:
(A) LENGTH: 12 amino acids
(B) TYPE: amino acid
(D) TOPOLOGY: unknown (ii) MOLECULE TYPE: peptide (xi) SEQUENCE DESCRIPTION: SEQ ID NO:113:

```
Arg Lys Ile Ser Gly Gln Ile Arg Gly Pro Gly Arg
1               5                   10
```

(2) INFORMATION FOR SEQ ID NO:114:

(i) SEQUENCE CHARACTERISTICS:
(A) LENGTH: 11 amino acids
(B) TYPE: amino acid (D) TOPOLOGY: unknown (ii) MOLECULE TYPE: peptide (xi) SEQUENCE DESCRIPTION: SEQ ID NO:114:

Thr Ile Gly Lys Ile Gly Asn Met Arg Gln Ala
1               5                   10

(2) INFORMATION FOR SEQ ID NO:115:

(i) SEQUENCE CHARACTERISTICS:
(A) LENGTH: 17 amino acids
(B) TYPE: amino acid
(D) TOPOLOGY: unknown (ii) MOLECULE TYPE: peptide (xi) SEQUENCE DESCRIPTION: SEQ ID NO:115:

Gly Gly Glu Phe Phe Tyr Cys Asn Ser Thr Gln Leu Phe Asn Ser Thr
1               5                   10                  15

Trp (2) INFORMATION FOR SEQ ID NO:116:

(i) SEQUENCE CHARACTERISTICS:
(A) LENGTH: 17 amino acids
(B) TYPE: amino acid
(D) TOPOLOGY: unknown (ii) MOLECULE TYPE: peptide (xi) SEQUENCE DESCRIPTION: SEQ ID NO:116:

Ile Thr Leu Pro Cys Arg Ile Lys Gln Ile Ile Asn Met Trp Gln Lys
1               5                   10                  15

Val (2) INFORMATION FOR SEQ ID NO:117:

(i) SEQUENCE CHARACTERISTICS:
(A) LENGTH: 19 amino acids
(B) TYPE: amino acid
(D) TOPOLOGY: unknown (ii) MOLECULE TYPE: peptide (xi) SEQUENCE DESCRIPTION: SEQ ID NO:117:

Lys Gln Ile Ile Asn Met Trp Gln Lys Val Gly Lys Ala Met Tyr Ala
1               5                   10                  15

Pro Pro Ile (2) INFORMATION FOR SEQ ID NO:118:

(i) SEQUENCE CHARACTERISTICS:
(A) LENGTH: 19 amino acids
(B) TYPE: amino acid
(D) TOPOLOGY: unknown (ii) MOLECULE TYPE: peptide (xi) SEQUENCE DESCRIPTION: SEQ ID NO:118:

Ala Pro Pro Ile Ser Gly Gln Ile Arg Cys Ser Ser Asn Ile Thr Gly
1               5                   10                  15

Leu Leu Leu (2) INFORMATION FOR SEQ ID NO:119:

( i ) SEQUENCE CHARACTERISTICS:
  ( A ) LENGTH: 15 amino acids
  ( B ) TYPE: amino acid
  ( D ) TOPOLOGY: unknown ( i i ) MOLECULE TYPE: peptide ( x i ) SEQUENCE DESCRIPTION: SEQ ID NO:119:

Ser Thr Met Gly Ala Ala Ser Met Thr Leu Thr Val Gln Ala Arg
1               5                   10                  15

( 2 ) INFORMATION FOR SEQ ID NO:120:

( i ) SEQUENCE CHARACTERISTICS:
    ( A ) LENGTH: 17 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:120:

Leu Gln Ala Arg Ile Leu Ala Val Glu Arg Tyr Leu Lys Asp Gln Gln
1               5                   10                  15

Leu ( 2 ) INFORMATION FOR SEQ ID NO:121:

( i ) SEQUENCE CHARACTERISTICS:
    ( A ) LENGTH: 12 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:121:

Leu Gly Ile Trp Gly Cys Ser Gly Lys Leu Ile Cys
1               5                   10

( 2 ) INFORMATION FOR SEQ ID NO:122:

( i ) SEQUENCE CHARACTERISTICS:
    ( A ) LENGTH: 10 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:122:

Asn Met Thr Trp Met Glu Trp Asp Arg Glu
1               5                   10

( 2 ) INFORMATION FOR SEQ ID NO:123:

( i ) SEQUENCE CHARACTERISTICS:
    ( A ) LENGTH: 15 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:123:

Ile Glu Glu Ser Gln Asn Gln Gln Glu Lys Asn Glu Gln Glu Leu
1               5                   10                  15

( 2 ) INFORMATION FOR SEQ ID NO:124:

( i ) SEQUENCE CHARACTERISTICS:
    ( A ) LENGTH: 21 amino acids
    ( B ) TYPE: amino acid (D) TOPOLOGY: unknown (ii) MOLECULE TYPE: peptide (xi) SEQUENCE DESCRIPTION: SEQ ID NO:124:

```
Arg Leu Val Asn Gly Ser Leu Ala Leu Ile Trp Asp Asp Leu Arg Ser
1               5                   10                  15
Leu Cys Leu Ser Phe
            20
```

(2) INFORMATION FOR SEQ ID NO:125:

(i) SEQUENCE CHARACTERISTICS:
    (A) LENGTH: 24 amino acids
    (B) TYPE: amino acid
    (D) TOPOLOGY: unknown (ii) MOLECULE TYPE: peptide (xi) SEQUENCE DESCRIPTION: SEQ ID NO:125:

```
Lys Tyr Trp Trp Asn Leu Leu Gln Tyr Trp Ser Gln Glu Leu Lys Asn
1               5                   10                  15
Ser Ala Val Ser Leu Leu Asn Ala
            20
```

(2) INFORMATION FOR SEQ ID NO:126:

(i) SEQUENCE CHARACTERISTICS:
    (A) LENGTH: 15 amino acids
    (B) TYPE: amino acid
    (D) TOPOLOGY: unknown (ii) MOLECULE TYPE: peptide (xi) SEQUENCE DESCRIPTION: SEQ ID NO:126:

```
Arg His Ile Pro Arg Arg Ile Arg Gln Gly Leu Glu Arg Ile Leu
1               5                   10                  15
```

(2) INFORMATION FOR SEQ ID NO:127:

(i) SEQUENCE CHARACTERISTICS:
    (A) LENGTH: 11 amino acids
    (B) TYPE: amino acid
    (D) TOPOLOGY: unknown (ii) MOLECULE TYPE: peptide (xi) SEQUENCE DESCRIPTION: SEQ ID NO:127:

```
Asn Val Thr Glu Asn Phe Asn Met Trp Lys Asn
1               5                   10
```

(2) INFORMATION FOR SEQ ID NO:128:

(i) SEQUENCE CHARACTERISTICS:
    (A) LENGTH: 13 amino acids
    (B) TYPE: amino acid
    (D) TOPOLOGY: unknown (ii) MOLECULE TYPE: peptide (xi) SEQUENCE DESCRIPTION: SEQ ID NO:128:

```
His Glu Asp Ile Ile Ser Leu Trp Asp Gln Ser Leu Lys
1               5                   10
```

(2) INFORMATION FOR SEQ ID NO:129:

(i) SEQUENCE CHARACTERISTICS:
    (A) LENGTH: 34 amino acids ( B ) TYPE: amino acid
( D ) TOPOLOGY: unknown ( i i ) MOLECULE TYPE: peptide ( x i ) SEQUENCE DESCRIPTION: SEQ ID NO:129:

```
Thr Arg Pro Asn Asn Asn Thr Arg Lys Ser Ile Arg Ile Gln Arg Gly
1               5                   10                  15

Pro Gly Arg Ala Phe Val Ile Ile Gly Lys Ile Gly Asn Met Arg Gln
            20                  25                  30

Ala His
```

( 2 ) INFORMATION FOR SEQ ID NO:130:

( i ) SEQUENCE CHARACTERISTICS:
( A ) LENGTH: 19 amino acids
( B ) TYPE: amino acid
( D ) TOPOLOGY: unknown ( i i ) MOLECULE TYPE: peptide ( x i ) SEQUENCE DESCRIPTION: SEQ ID NO:130:

```
Thr Gly Asn Ile Thr Leu Pro Cys Arg Ile Lys Gln Val Val Arg Thr
1               5                   10                  15

Trp Gln Gly
```

( 2 ) INFORMATION FOR SEQ ID NO:131:

( i ) SEQUENCE CHARACTERISTICS:
( A ) LENGTH: 24 amino acids
( B ) TYPE: amino acid
( D ) TOPOLOGY: unknown ( i i ) MOLECULE TYPE: peptide ( x i ) SEQUENCE DESCRIPTION: SEQ ID NO:131:

```
Cys Arg Ile Lys Gln Ile Ile Asn Met Trp Gln Lys Val Gly Lys Ala
1               5                   10                  15

Met Tyr Ala Pro Pro Ile Ser Gly
            20
```

( 2 ) INFORMATION FOR SEQ ID NO:132:

( i ) SEQUENCE CHARACTERISTICS:
( A ) LENGTH: 23 amino acids
( B ) TYPE: amino acid
( D ) TOPOLOGY: unknown ( i i ) MOLECULE TYPE: peptide ( x i ) SEQUENCE DESCRIPTION: SEQ ID NO:132:

```
Glu Leu Tyr Lys Tyr Lys Val Val Lys Ile Glu Pro Leu Gly Val Ala
1               5                   10                  15

Pro Thr Lys Ala Lys Arg Arg
            20
```

( 2 ) INFORMATION FOR SEQ ID NO:133:

( i ) SEQUENCE CHARACTERISTICS:
( A ) LENGTH: 12 amino acids
( B ) TYPE: amino acid
( D ) TOPOLOGY: unknown ( i i ) MOLECULE TYPE: peptide ( x i ) SEQUENCE DESCRIPTION: SEQ ID NO:133:

```
    Val  Val  Gln  Arg  Glu  Lys  Arg  Ala  Val  Gly  Ile  Gly
    1              5                        10
```

( 2 ) INFORMATION FOR SEQ ID NO:134:

( i ) SEQUENCE CHARACTERISTICS:
        ( A ) LENGTH: 24 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:134:

```
    Tyr  Asn  Lys  Arg  Lys  Arg  Ile  His  Ile  Gln  Arg  Gly  Pro  Gly  Arg  Ala
    1              5                        10                            15

Phe  Tyr  Thr  Thr  Lys  Asn  Ile  Ile
                   20
```

( 2 ) INFORMATION FOR SEQ ID NO:135:

( i ) SEQUENCE CHARACTERISTICS:
        ( A ) LENGTH: 18 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:135:

```
    Val  Ile  Thr  Gln  Ala  Cys  Pro  Lys  Val  Ser  Phe  Glu  Pro  Ile  Pro  Ile
    1              5                        10                            15

His  Tyr
```

( 2 ) INFORMATION FOR SEQ ID NO:136:

( i ) SEQUENCE CHARACTERISTICS:
        ( A ) LENGTH: 16 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:136:

```
    Cys  Ala  Pro  Ala  Gly  Phe  Ala  Ile  Leu  Lys  Cys  Asn  Asp  Lys  Lys  Phe
    1              5                        10                            15
```

( 2 ) INFORMATION FOR SEQ ID NO:137:

( i ) SEQUENCE CHARACTERISTICS:
        ( A ) LENGTH: 19 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:137:

```
    Cys  Asn  Asn  Lys  Thr  Phe  Asn  Gly  Thr  Gly  Pro  Cys  Thr  Asn  Val  Ser
    1              5                        10                            15

Thr  Val  Gln
```

( 2 ) INFORMATION FOR SEQ ID NO:138:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:138:

Gly Gly Gly Asp Met Arg Asp Asn Trp Arg Ser Glu Leu Tyr Lys
1               5                   10                  15

( 2 ) INFORMATION FOR SEQ ID NO:139:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:139:

Phe Asn Ser Thr Trp Phe Asn Ser Thr Trp Ser Thr Lys Gly Ser
1               5                   10                  15

( 2 ) INFORMATION FOR SEQ ID NO:140:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:140:

Glu Pro Ile Pro Ile His Tyr Cys Ala Pro Ala Gly Phe Ala Ile
1               5                   10                  15

( 2 ) INFORMATION FOR SEQ ID NO:141:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:141:

Arg Gln Ala His Cys Asn Ile Ser Arg Ala Lys Trp Asn Asn Thr
1               5                   10                  15

( 2 ) INFORMATION FOR SEQ ID NO:142:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:142:

Asn Phe Thr Asp Asn Ala Lys Thr Ile Ile Val Gln Leu Asn Gln
1               5                   10                  15

( 2 ) INFORMATION FOR SEQ ID NO:143:

( i ) SEQUENCE CHARACTERISTICS:
        ( A ) LENGTH: 22 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:143:

Gln Cys Thr His Gly Ile Arg Pro Val Val Ser Thr Gln Leu Leu Leu
1               5                   10                  15

```
        Asn  Gly  Ser  Leu  Ala  Glu
                       20
```

( 2 ) INFORMATION FOR SEQ ID NO:144:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:144:

```
   Lys  Gln  Ile  Ala  Asp  Ser  Lys  Leu  Arg  Glu  Gln  Phe  Gly  Asn  Asn
   1                  5                        10                       15
```

( 2 ) INFORMATION FOR SEQ ID NO:145:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:145:

```
   Phe  Lys  Gln  Ser  Ser  Gly  Gly  Asp  Pro  Glu  Ile  Val  Thr  His  Ser
   1                  5                        10                       15
```

( 2 ) INFORMATION FOR SEQ ID NO:146:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:146:

```
   Ser  Thr  Lys  Gly  Ser  Asn  Asn  Thr  Glu  Gly  Ser  Asp  Thr  Ile  Thr
   1                  5                        10                       15
```

( 2 ) INFORMATION FOR SEQ ID NO:147:

( i ) SEQUENCE CHARACTERISTICS:
        ( A ) LENGTH: 21 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:147:

```
   Cys  Thr  His  Gly  Ile  Arg  Pro  Val  Val  Ser  Thr  Gln  Leu  Leu  Leu  Asn
   1                  5                        10                       15

Gly  Ser  Leu  Ala  Glu
                    20
```

( 2 ) INFORMATION FOR SEQ ID NO:148:

( i ) SEQUENCE CHARACTERISTICS:
        ( A ) LENGTH: 29 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:148:

```
   Arg  Glu  Gln  Phe  Gly  Asn  Asn  Lys  Thr  Ile  Ile  Phe  Lys  Gln  Ser  Ser
   1                  5                        10                       15
```

Gly Gly Asp Pro Glu Ile Val Thr His Ser Phe Asn Cys
             20                      25

( 2 ) INFORMATION FOR SEQ ID NO:149:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:149:

Gly Cys Ser Gly Lys Leu Ile Cys
1               5

( 2 ) INFORMATION FOR SEQ ID NO:150:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:150:

Cys Ser Gly Lys Leu Ile Cys Thr
1               5

( 2 ) INFORMATION FOR SEQ ID NO:151:

( i ) SEQUENCE CHARACTERISTICS:
        ( A ) LENGTH: 26 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:151:

Arg Ile Leu Ala Val Glu Arg Tyr Leu Lys Asp Gln Gln Leu Leu Gly
1               5                   10                  15
Ile Trp Gly Cys Ser Gly Lys Leu Ile Cys
             20                      25

( 2 ) INFORMATION FOR SEQ ID NO:152:

( i ) SEQUENCE CHARACTERISTICS:
        ( A ) LENGTH: 23 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:152:

Leu Glu Leu Asp Lys Trp Ala Ser Leu Trp Asn Trp Phe Asn Ile Thr
1               5                   10                  15
Asn Trp Leu Trp Tyr Ile Lys
             20

( 2 ) INFORMATION FOR SEQ ID NO:153:

( i ) SEQUENCE CHARACTERISTICS:
        ( A ) LENGTH: 17 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:153:

Asn Ala Ser Trp Ser Asn Lys Ser Leu Glu Gln Ile Trp Asn Asn Met
1               5                   10                  15

Thr ( 2 ) INFORMATION FOR SEQ ID NO:154:

( i ) SEQUENCE CHARACTERISTICS:
( A ) LENGTH: 20 amino acids
( B ) TYPE: amino acid
( D ) TOPOLOGY: unknown ( i i ) MOLECULE TYPE: peptide ( x i ) SEQUENCE DESCRIPTION: SEQ ID NO:154:

Ser Leu Ile Glu Glu Ser Gln Asn Gln Gln Glu Lys Asn Glu Gln Glu
1               5                   10                  15

Leu Leu Glu Leu
            20

( 2 ) INFORMATION FOR SEQ ID NO:155:

( i ) SEQUENCE CHARACTERISTICS:
( A ) LENGTH: 19 amino acids
( B ) TYPE: amino acid
( D ) TOPOLOGY: unknown ( i i ) MOLECULE TYPE: peptide ( x i ) SEQUENCE DESCRIPTION: SEQ ID NO:155:

Ser Val Val Asn Arg Val Arg Gln Gly Tyr Ser Pro Leu Ser Phe Gln
1               5                   10                  15

Thr His Leu ( 2 ) INFORMATION FOR SEQ ID NO:156:

( i ) SEQUENCE CHARACTERISTICS:
( A ) LENGTH: 21 amino acids
( B ) TYPE: amino acid
( D ) TOPOLOGY: unknown ( i i ) MOLECULE TYPE: peptide ( x i ) SEQUENCE DESCRIPTION: SEQ ID NO:156:

Arg Leu Val Asn Gly Ser Leu Ala Leu Ile Trp Asp Asp Leu Arg Ser
1               5                   10                  15

Leu Cys Leu Phe Ser
            20

( 2 ) INFORMATION FOR SEQ ID NO:157:

( i ) SEQUENCE CHARACTERISTICS:
( A ) LENGTH: 24 amino acids
( B ) TYPE: amino acid
( D ) TOPOLOGY: unknown ( i i ) MOLECULE TYPE: peptide ( x i ) SEQUENCE DESCRIPTION: SEQ ID NO:157:

Gln Ala Arg Gln Leu Leu Ser Gly Ile Val Gln Gln Gln Asn Asn Leu
1               5                   10                  15

Leu Arg Ala Ile Glu Ala Gln Gln
            20

( 2 ) INFORMATION FOR SEQ ID NO:158:

(  i  ) SEQUENCE CHARACTERISTICS:
       ( A ) LENGTH: 15 amino acids
       ( B ) TYPE: amino acid
       ( D ) TOPOLOGY: unknown (  i i  ) MOLECULE TYPE: peptide (  x i  ) SEQUENCE DESCRIPTION: SEQ ID NO:158:

Leu Ser Leu Gln Thr Arg Pro Pro Val Pro Arg Gly Pro Asp Arg
1               5                   10                  15

( 2 ) INFORMATION FOR SEQ ID NO:159:

(  i  ) SEQUENCE CHARACTERISTICS:
       ( A ) LENGTH: 15 amino acids
       ( B ) TYPE: amino acid
       ( D ) TOPOLOGY: unknown (  i i  ) MOLECULE TYPE: peptide (  x i  ) SEQUENCE DESCRIPTION: SEQ ID NO:159:

Asp Thr Ser Gly Arg Leu Val His Gly Phe Leu Ala Ile Ile Trp
1               5                   10                  15

( 2 ) INFORMATION FOR SEQ ID NO:160:

(  i  ) SEQUENCE CHARACTERISTICS:
       ( A ) LENGTH: 15 amino acids
       ( B ) TYPE: amino acid
       ( D ) TOPOLOGY: unknown (  i i  ) MOLECULE TYPE: peptide (  x i  ) SEQUENCE DESCRIPTION: SEQ ID NO:160:

Trp Val Asp Leu Arg Ser Leu Phe Leu Phe Ser Tyr His His Arg
1               5                   10                  15

( 2 ) INFORMATION FOR SEQ ID NO:161:

(  i  ) SEQUENCE CHARACTERISTICS:
       ( A ) LENGTH: 24 amino acids
       ( B ) TYPE: amino acid
       ( D ) TOPOLOGY: unknown (  i i  ) MOLECULE TYPE: peptide (  x i  ) SEQUENCE DESCRIPTION: SEQ ID NO:161:

Val Thr Ile Glu Pro Leu Gly Val Ala Pro Pro Thr Lys Ala Lys Arg
1               5                   10                  15

Arg Val Val Gln Arg Glu Lys Arg
                20

( 2 ) INFORMATION FOR SEQ ID NO:162:

(  i  ) SEQUENCE CHARACTERISTICS:
       ( A ) LENGTH: 32 amino acids
       ( B ) TYPE: amino acid
       ( D ) TOPOLOGY: unknown (  i i  ) MOLECULE TYPE: peptide (  x i  ) SEQUENCE DESCRIPTION: SEQ ID NO:162:

Ala Tyr Gly Ile Gly Ala Leu Phe Leu Gly Phe Leu Gly Ala Ala Gly
1               5                   10                  15

Ser Thr Met Gly Ala Ala Ser Met Thr Leu Thr Val Gln Ala Arg Cys
                20                  25                  30

( 2 ) INFORMATION FOR SEQ ID NO:163:

( i ) SEQUENCE CHARACTERISTICS:
        ( A ) LENGTH: 11 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:163:

```
Phe Leu Gly Phe Leu Gly Ala Ala Gly Ser Thr
1               5                   10
```

( 2 ) INFORMATION FOR SEQ ID NO:164:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:164:

```
Val Val Gln Arg Glu Lys Arg Ala Ala Ile Gly Ala Ile Phe Leu
1               5                   10                  15
```

( 2 ) INFORMATION FOR SEQ ID NO:165:

( i ) SEQUENCE CHARACTERISTICS:
        ( A ) LENGTH: 16 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:165:

```
His Met Leu Gln Leu Thr Val Trp Gly Ile Lys Gln Leu Gln Ala Arg
1               5                   10                  15
```

( 2 ) INFORMATION FOR SEQ ID NO:166:

( i ) SEQUENCE CHARACTERISTICS:
        ( A ) LENGTH: 19 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:166:

```
Ser Leu Asp Asp Ile Trp Asn Asn Met Thr Trp Met Gln Trp Glu Arg
1               5                   10                  15

Glu Ile Asp
```

( 2 ) INFORMATION FOR SEQ ID NO:167:

( i ) SEQUENCE CHARACTERISTICS:
        ( A ) LENGTH: 13 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:167:

```
Asn Tyr Thr Ser Leu Ile Tyr Ser Leu Leu Glu Lys Ser
1               5                   10
```

( 2 ) INFORMATION FOR SEQ ID NO:168:

( i ) SEQUENCE CHARACTERISTICS:

(A) LENGTH: 17 amino acids
(B) TYPE: amino acid
(D) TOPOLOGY: unknown (ii) MOLECULE TYPE: peptide (xi) SEQUENCE DESCRIPTION: SEQ ID NO:168:

```
Val Leu Ala Val Glu Arg Tyr Leu Lys Asp Gln Gln Leu Leu Gly Phe
1               5                   10                  15
Trp
```

(2) INFORMATION FOR SEQ ID NO:169:

(i) SEQUENCE CHARACTERISTICS:
(A) LENGTH: 10 amino acids
(B) TYPE: amino acid
(D) TOPOLOGY: unknown (ii) MOLECULE TYPE: peptide (xi) SEQUENCE DESCRIPTION: SEQ ID NO:169:

```
Met Gly Ala Ala Ser Val Thr Leu Thr Val
1               5                   10
```

(2) INFORMATION FOR SEQ ID NO:170:

(i) SEQUENCE CHARACTERISTICS:
(A) LENGTH: 14 amino acids
(B) TYPE: amino acid
(D) TOPOLOGY: unknown (ii) MOLECULE TYPE: peptide (xi) SEQUENCE DESCRIPTION: SEQ ID NO:170:

```
Tyr Ile Lys Ile Phe Ile Met Ile Val Gly Gly Leu Val Gly
1               5                   10
```

(2) INFORMATION FOR SEQ ID NO:171:

(i) SEQUENCE CHARACTERISTICS:
(A) LENGTH: 15 amino acids
(B) TYPE: amino acid
(D) TOPOLOGY: unknown (ii) MOLECULE TYPE: peptide (xi) SEQUENCE DESCRIPTION: SEQ ID NO:171:

```
His Ile Pro Thr Arg Ile Arg Gln Gly Leu Glu Arg Ala Leu Leu
1               5                   10                  15
```

(2) INFORMATION FOR SEQ ID NO:172:

(i) SEQUENCE CHARACTERISTICS:
(A) LENGTH: 13 amino acids
(B) TYPE: amino acid
(D) TOPOLOGY: unknown (ii) MOLECULE TYPE: peptide (xi) SEQUENCE DESCRIPTION: SEQ ID NO:172:

```
Ser Asn Lys Ser Leu Glu Gln Ile Trp Asn Asn Met Thr
1               5                   10
```

(2) INFORMATION FOR SEQ ID NO:173:

(i) SEQUENCE CHARACTERISTICS:
(A) LENGTH: 24 amino acids
(B) TYPE: amino acid
(D) TOPOLOGY: unknown ( i i ) MOLECULE TYPE: peptide ( x i ) SEQUENCE DESCRIPTION: SEQ ID NO:173:

```
Lys Tyr Trp Trp Asn Leu Leu Gln Tyr Trp Ser Gln Glu Leu Lys Asn
1               5                   10                  15
Ser Ala Val Ser Leu Leu Asn Ala
            20
```

( 2 ) INFORMATION FOR SEQ ID NO:174:

( i ) SEQUENCE CHARACTERISTICS:
        ( A ) LENGTH: 18 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:174:

```
Asp Arg Pro Glu Gly Ile Glu Glu Glu Gly Gly Glu Arg Asp Arg Asp
1               5                   10                  15
Arg Ser
```

( 2 ) INFORMATION FOR SEQ ID NO:175:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:175:

```
Glu Gly Thr Asp Arg Val Ile Glu
1               5
```

( 2 ) INFORMATION FOR SEQ ID NO:176:

( i ) SEQUENCE CHARACTERISTICS:
        ( A ) LENGTH: 10 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:176:

```
Asn Met Thr Trp Met Glu Trp Asp Arg Glu
1               5                   10
```

( 2 ) INFORMATION FOR SEQ ID NO:177:

( i ) SEQUENCE CHARACTERISTICS:
        ( A ) LENGTH: 7 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:177:

```
Lys Arg Ala Val Gly Ile Gly
1               5
```

( 2 ) INFORMATION FOR SEQ ID NO:178:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:178:

Trp Leu Trp Tyr Ile Lys Leu Phe Ile Met Ile Val Gly Gly Leu Val
1               5                   10                  15

Gly Leu Arg Ile
            20

( 2 ) INFORMATION FOR SEQ ID NO:179:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:179:

Lys Ser Ile His Ile Gly Pro Gly Arg Ala Phe Tyr Thr Thr Gly
1               5                   10                  15

( 2 ) INFORMATION FOR SEQ ID NO:180:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:180:

Lys Ser Ile Pro Met Gly Pro Gly Lys Ala Phe Tyr Ala Thr Gly
1               5                   10                  15

( 2 ) INFORMATION FOR SEQ ID NO:181:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:181:

Lys Arg Ile His Ile Gly Pro Gly Arg Ala Phe Tyr Thr Thr Lys
1               5                   10                  15

( 2 ) INFORMATION FOR SEQ ID NO:182:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:182:

Lys Ser Ile Thr Lys Gly Pro Gly Arg Val Ile Tyr Ala Thr Gly
1               5                   10                  15

( 2 ) INFORMATION FOR SEQ ID NO:183:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:183:

Lys Ser Ile Tyr Ile Gly Pro Gly Arg Ala Phe His Thr Thr Gly
1               5                   10                  15

( 2 ) INFORMATION FOR SEQ ID NO:184:

( i ) SEQUENCE CHARACTERISTICS:
         ( A ) LENGTH: 15 amino acids
         ( B ) TYPE: amino acid
         ( D ) TOPOLOGY: unknown ( i i ) MOLECULE TYPE: peptide ( x i ) SEQUENCE DESCRIPTION: SEQ ID NO:184:

Thr Ser Ile Thr Ile Gly Pro Gly Gln Val Phe Tyr Arg Thr Gly
1               5                   10                  15

( 2 ) INFORMATION FOR SEQ ID NO:185:

( i ) SEQUENCE CHARACTERISTICS:
         ( A ) LENGTH: 15 amino acids
         ( B ) TYPE: amino acid
         ( D ) TOPOLOGY: unknown ( i i ) MOLECULE TYPE: peptide ( x i ) SEQUENCE DESCRIPTION: SEQ ID NO:185:

Lys Gly Ile Arg Ile Gly Pro Gly Arg Ala Val Tyr Ala Ala Glu
1               5                   10                  15

( 2 ) INFORMATION FOR SEQ ID NO:186:

( i ) SEQUENCE CHARACTERISTICS:
         ( A ) LENGTH: 17 amino acids
         ( B ) TYPE: amino acid
         ( D ) TOPOLOGY: unknown ( i i ) MOLECULE TYPE: peptide ( x i ) SEQUENCE DESCRIPTION: SEQ ID NO:186:

Cys Gly Thr Thr Tyr Phe Ala Arg Gly Pro Gly Ile His Ile Ser Lys
1               5                   10                  15

Cys ( 2 ) INFORMATION FOR SEQ ID NO:187:

( i ) SEQUENCE CHARACTERISTICS:
         ( A ) LENGTH: 17 amino acids
         ( B ) TYPE: amino acid
         ( D ) TOPOLOGY: unknown ( i i ) MOLECULE TYPE: peptide ( x i ) SEQUENCE DESCRIPTION: SEQ ID NO:187:

Cys Gly Thr Arg Tyr Phe Val Gln Gly Pro Gly Ile Thr Ile Ser Thr
1               5                   10                  15

Cys ( 2 ) INFORMATION FOR SEQ ID NO:188:

( i ) SEQUENCE CHARACTERISTICS:
         ( A ) LENGTH: 17 amino acids
         ( B ) TYPE: amino acid
         ( D ) TOPOLOGY: unknown ( i i ) MOLECULE TYPE: peptide ( x i ) SEQUENCE DESCRIPTION: SEQ ID NO:188:

Cys Glu Ala Ala Tyr Val Ala Arg Gly Pro Gly Ile Arg Ile Gly Lys
1               5                   10                  15

Cys ( 2 ) INFORMATION FOR SEQ ID NO:189:

( i ) SEQUENCE CHARACTERISTICS:
       ( A ) LENGTH: 33 amino acids
       ( B ) TYPE: amino acid
       ( D ) TOPOLOGY: unknown ( i i ) MOLECULE TYPE: peptide ( x i ) SEQUENCE DESCRIPTION: SEQ ID NO:189:

His Ala Gln Arg Ile Thr Gly Ile Ile Asn Lys Thr Thr Tyr Phe Ala
1               5                   10                  15

Arg Gly Pro Gly Ile His Ile Arg Lys Arg Lys Asn Tyr Asn Pro Arg
                20                  25                  30

Thr ( 2 ) INFORMATION FOR SEQ ID NO:190:

( i ) SEQUENCE CHARACTERISTICS:
       ( A ) LENGTH: 35 amino acids
       ( B ) TYPE: amino acid
       ( D ) TOPOLOGY: unknown ( i i ) MOLECULE TYPE: peptide ( x i ) SEQUENCE DESCRIPTION: SEQ ID NO:190:

Cys His Ala Gln Arg Ile Thr Gly Ile Ile Asn Lys Thr Thr Tyr Phe
1               5                   10                  15

Ala Arg Gly Pro Gly Ile His Ile Arg Lys Arg Lys Asn Tyr Asn Pro
                20                  25                  30

Arg Thr Cys
        35

( 2 ) INFORMATION FOR SEQ ID NO:191:

( i ) SEQUENCE CHARACTERISTICS:
       ( A ) LENGTH: 20 amino acids
       ( B ) TYPE: amino acid
       ( D ) TOPOLOGY: unknown ( i i ) MOLECULE TYPE: peptide ( x i ) SEQUENCE DESCRIPTION: SEQ ID NO:191:

Thr Gly Asp Ile Ile Thr Leu Pro Cys Arg Ile Lys Gln Ile Ile Asn
1               5                   10                  15

Arg Trp Gln Val
                20

( 2 ) INFORMATION FOR SEQ ID NO:192:

( i ) SEQUENCE CHARACTERISTICS:
       ( A ) LENGTH: 16 amino acids
       ( B ) TYPE: amino acid
       ( D ) TOPOLOGY: unknown ( i i ) MOLECULE TYPE: peptide ( x i ) SEQUENCE DESCRIPTION: SEQ ID NO:192:

Ser Leu Trp Asp Gln Ser Leu Lys Pro Cys Val Lys Thr Asp Leu Gly
1               5                   10                  15

( 2 ) INFORMATION FOR SEQ ID NO:193:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:193:

```
Cys Thr Thr Ala Val Pro Trp Asn Ala Ser Trp Ser Asn Lys Ser
1               5                   10                  15
```

( 2 ) INFORMATION FOR SEQ ID NO:194:

( i ) SEQUENCE CHARACTERISTICS:
        ( A ) LENGTH: 35 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:194:

```
Lys Gln Ile Ile Asn Met Trp Gln Glu Val Gly Lys Ala Met Tyr Ala
1               5                   10                  15
Cys Thr Arg Pro Asn Asn Asn Thr Arg Lys Ser Ile Arg Ile Gln Arg
                20                  25                  30
Gly Pro Gly
        35
```

( 2 ) INFORMATION FOR SEQ ID NO:195:

( i ) SEQUENCE CHARACTERISTICS:
        ( A ) LENGTH: 19 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:195:

```
Thr Gly Pro Cys Thr Asn Val Ser Thr Val Gln Cys Thr His Gly Ile
1               5                   10                  15
Arg Pro Val
```

( 2 ) INFORMATION FOR SEQ ID NO:196:

( i ) SEQUENCE CHARACTERISTICS:
        ( A ) LENGTH: 18 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:196:

```
Ser Thr Gln Leu Leu Leu Asn Gly Ser Leu Ala Glu Glu Glu Val Val
1               5                   10                  15
Ile Arg
```

( 2 ) INFORMATION FOR SEQ ID NO:197:

( i ) SEQUENCE CHARACTERISTICS:
        ( A ) LENGTH: 13 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:197:

Ile Glu Val Leu Gln Arg Ala Gly Arg Ala Ile Leu His
1               5                           10